US012650426B2

(12) United States Patent
Choi et al.

(10) Patent No.: US 12,650,426 B2
(45) Date of Patent: Jun. 9, 2026

(54) AUTOMATED LIQUID-PHASE IMMUNOASSAY APPARATUS AND METHOD THEREFOR

(71) Applicant: BODITECH MED INC., Gangwon-Do (KR)

(72) Inventors: Eui Yul Choi, Gangwon-do (KR); Hoo Don Joo, Gangwon-do (KR); Hyung Hoon Kim, Gangwon-do (KR); Chu Hyun Cho, Gangwon-do (KR); Uk Bin Im, Gangwon-Do (KR); Young Jin Oh, Gangwon-do (KR); Youn Tae Im, Gangwon-do (KR); Ji Woon Jung, Gangwon-do (KR)

(73) Assignee: BODITECH MED INC., Gangwon-Do (KR)

( * ) Notice: Subject to any disclaimer, the term of this patent is extended or adjusted under 35 U.S.C. 154(b) by 1178 days.

(21) Appl. No.: 17/056,132

(22) PCT Filed: Jul. 19, 2019

(86) PCT No.: PCT/KR2019/008920
§ 371 (c)(1),
(2) Date: Nov. 17, 2020

(87) PCT Pub. No.: WO2020/027470
PCT Pub. Date: Feb. 6, 2020

(65) Prior Publication Data
US 2021/0311033 A1     Oct. 7, 2021

(30) Foreign Application Priority Data
Aug. 3, 2018     (KR) ........................ 10-2018-0090983

(51) Int. Cl.
| *G01N 33/537* | (2006.01) |
| *G01N 21/64* | (2006.01) |
| *G01N 21/76* | (2006.01) |
| *G01N 33/00* | (2006.01) |
| *G01N 33/10* | (2006.01) |
(Continued)

(52) U.S. Cl.
CPC ..... *G01N 33/5375* (2013.01); *G01N 21/6428* (2013.01); *G01N 21/76* (2013.01);
(Continued)

(58) Field of Classification Search
CPC ............ B01L 3/502; B01L 2300/0654; B01L 2300/0663; G01N 21/6428; G01N 21/76;
(Continued)

(56) References Cited

U.S. PATENT DOCUMENTS 8,222,048 B2    7/2012  Fritchie et al.
2008/0241914 A1*   10/2008  Roh ...................... B01L 3/0289
                                                                435/307.1
(Continued)

FOREIGN PATENT DOCUMENTS

JP          H0949841 A       2/1997
KR          20120027359 A    3/2012
(Continued)

OTHER PUBLICATIONS

International Search Report issued by ISA/KR in connection with PCT/KR2019/008920 on Oct. 29, 2019.
(Continued)

*Primary Examiner* — Matthew D Krcha
*Assistant Examiner* — Austin Q Le
(74) *Attorney, Agent, or Firm* — Klintworth & Rozenblat LLP

(57)    ABSTRACT

The present invention relates to an ELISA-based, liquid-phase immunoassay apparatus optimized for detecting particular ingredients contained in a biological sample, etc., and a method therefor.

6 Claims, 25 Drawing Sheets

(51) Int. Cl.

| | | |
|---|---|---|
| *G01N 35/00* | (2006.01) | |
| *G01N 35/04* | (2006.01) | |
| *G01N 35/10* | (2006.01) | |
| *B01L 3/00* | (2006.01) | |

(52) U.S. Cl.
CPC ......... *G01N 35/0098* (2013.01); *G01N 35/04* (2013.01); *G01N 35/10* (2013.01); *G01N 35/1011* (2013.01); *B01L 3/502* (2013.01); *B01L 2300/0654* (2013.01); *B01L 2300/0663* (2013.01); *G01N 2035/00564* (2013.01); *G01N 2035/0401* (2013.01); *G01N 2035/103* (2013.01)

(58) Field of Classification Search
CPC ............... G01N 21/84; G01N 33/5375; G01N 35/00029; G01N 35/0098; G01N 35/04; G01N 35/10; G01N 35/1011; G01N 2035/00564; G01N 2035/0401; G01N 2035/103
See application file for complete search history.

(56) References Cited

U.S. PATENT DOCUMENTS

| | | | |
|---|---|---|---|
| 2011/0009608 A1* | 1/2011 | Kim .................... G01N 35/1074 | |
| | | | 536/25.41 |
| 2011/0124028 A1 | 5/2011 | Robinson et al. | |
| 2012/0309104 A1* | 12/2012 | Uematsu ............... B01L 3/0275 | |
| | | | 436/174 |
| 2015/0111287 A1* | 4/2015 | Rawle .................... C12Q 1/701 | |
| | | | 422/69 |
| 2015/0185116 A1* | 7/2015 | Brisebrat ............. G01N 35/026 | |
| | | | 83/660 |
| 2018/0128715 A1 | 5/2018 | Kim et al. | |

FOREIGN PATENT DOCUMENTS

| | | | | |
|---|---|---|---|---|
| KR | 20150056479 | A | | 5/2015 |
| KR | 20160000001 | A | * | 1/2016 |
| KR | 20160134542 | A | * | 11/2016 |
| KR | 101865615 | B1 | | 6/2018 |
| KR | 20180079150 | A | | 7/2018 |
| KR | 20180090201 | A | | 8/2018 |
| WO | 2015170844 | A1 | | 11/2015 |

OTHER PUBLICATIONS

Automated Immunoprecipitation in 40 min using Dynabeads and KingFisher Flex, Thermo Fisher Scientific, Jun. 6, 2017, https://www.youtube.com/watch?v=AJ7c0vhbr04.

Thermo Scientific KingFisher 1-15 Flex User Manual, Dec. 31, 2010, https://static.thermoscientific.com/images/D01475-.pdf.

* cited by examiner

20

30

30   20

10

12   13a   13b   13c   13d   14   15a   15b   15c   16

S710 — accomodating a cubette to a device

S720 — mounting a dispensing tip and a washing tip to a device

S730 — moving to a start position of a holder

S740 — opening a sealing film of a cuvette

S750 — fixing a dispensing tip to a lower part of a collection arm

S760 — distributing and dispensing a sample by means of a dispensing tip

S770 — incubation of a sample

S780 — washing a sample

S790 — optical inspection

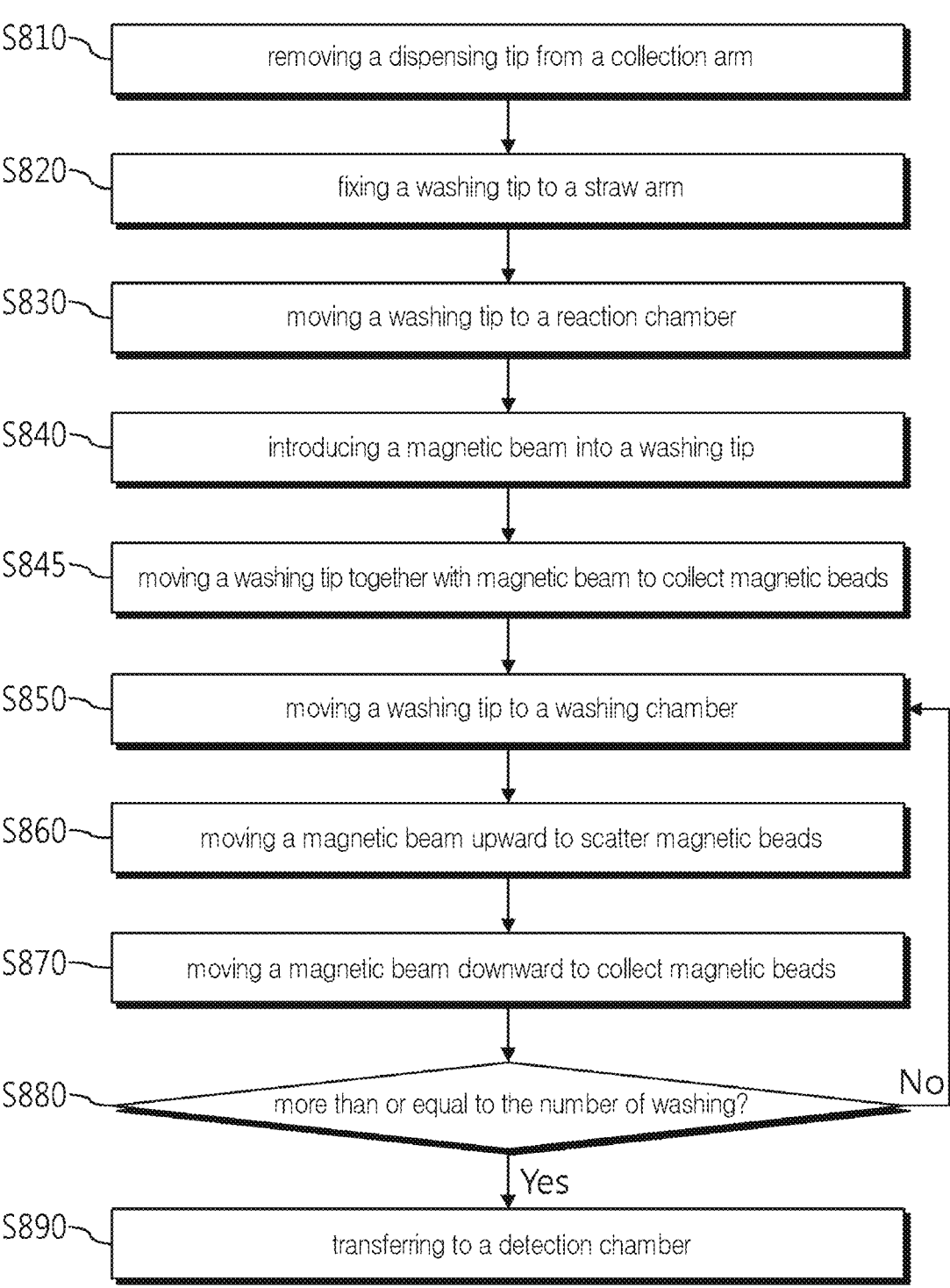

S810 — removing a dispensing tip from a collection arm

S820 — fixing a washing tip to a straw arm

S830 — moving a washing tip to a reaction chamber

S840 — introducing a magnetic beam into a washing tip

S845 — moving a washing tip together with magnetic beam to collect magnetic beads S850 — moving a washing tip to a washing chamber S860 — moving a magnetic beam upward to scatter magnetic beads S870 — moving a magnetic beam downward to collect magnetic beads S880 — more than or equal to the number of washing?    No Yes S890 — transferring to a detection chamber

FIG. 18

S910 — disposing a standard block above an optical reader

S920 — reading an optical signal of a standard block

S930 — disposing a detection chamber above an optical reader

S940 — reading an optical signal of a detection chamber

S950 — correcting variations of a standard block and a detection chamber (a)

(b)

(c)

(d)

AUTOMATED LIQUID-PHASE IMMUNOASSAY APPARATUS AND METHOD THEREFOR

TECHNICAL FIELD

The present invention relates to a device or system for detecting particular ingredients contained in a biological sample by ELISA (Enzyme Linked Immuno Sorbent Assay)-based liquid immunoassay and a method therefor.

BACKGROUND ART

As medicine, biotechnology and various related technologies develop, the inspections have been widely performed to detect various molecular indicators such as blood cells, genes, proteins, antigens, pathogens, etc. in predetermined biological samples such as urine and blood. The inspection process generally comprises the steps of: taking a sample, reacting the sample with a predetermined reagent suitable for the desired indicator, and observing and analyzing the changes that occur. In this way, the various molecular indicators included in a sample can be analyzed qualitatively and/or quantitatively, so that the information on diagnosis, progress or prognosis of disease can be obtained.

One of the techniques widely used in this inspection process is an immunoassay technique called EIA (Enzyme ImmunoAssay) based on specific binding between antigens and antibodies. This includes color change measurement method (chromogenic or colorimetric) to measure the color reaction by absorbance, chemiluminescence method and fluorescence method, depending on the type of substrate used for detection of the analyte. It also includes a sandwich-type immunoassay or competition immunoassay, also called Enzyme Linked Immunosorbent Assay, depending on the assay.

In such assays, removal of non-specific reactants is desirable for high sensitivity detection of high specificity regardless of how to use. That is, after the reaction between the reagent and the sample in the inspection process, it is required to purify the reaction product for accurate detection of the reaction product. In many cases, however, the detection of the reactants requires to use membranes such as nitrocellulose, or two-dimensional flat plates. But, the use of such membranes or plates makes it difficult to remove non-specific reactants as well as limits the reaction area.

The most effective method for removing non-specific reactants is physical washing or purification. Accordingly, there is a need for the development of a device/system in which a plurality of inspections for the reaction of quantitative samples and reagents, the physical purification of reaction product, and the detection, reading and analysis can be performed accurately and quickly under one integrated system.

DOCUMENTS OF RELATED ART

Patent Literature

Patent Literature 1. KR Patent Publication No. 10-2012-0027359 (published on Mar. 21, 2012)
Patent Literature 2. KR Patent Publication No. 10-2016-0000001 (published on Jan. 4, 2017)
Patent Literature 3. KR Patent Publication No. 10-2018-0079150 (published on Jul. 10, 2018)

DISCLOSURE

Technical Problem

The present invention provides device, system and method using a liquid enzyme-linked immunoassay, which are optimized for the reaction of samples and reagents, the purification of the reaction product and the integrated performance of detection, reading and analysis of the reaction product.

The objective of the present invention is not limited to the above-mentioned objective, and other objectives of the present invention not mentioned above will be clearly understood by those skilled in the art from the following description

Technical Solution

The present invention for achieving the above-mentioned objectives provides an automated liquid immunoassay method including steps of: (a) collecting magnetic beads in sample solution onto the surface of a washing tip by introducing the washing tip into which a magnetic beam is inserted into the sample solution containing the magnetic beads; (b) moving the washing tip onto a surface of which the magnetic beads are collected to a washing solution so as to introducing the magnetic beads into the washing solution; (c) moving the magnetic beam vertically upward and downward with a driving motor connected to the magnetic beam, and moving the washing tip vertically upward and downward several times so as to scatter the magnetic beads collected onto the washing tip in the washing solution; and (d) collecting the magnetic beads in the washing solution by inserting the magnetic beam into the washing tip.

Preferably, the step (d) of collecting the magnetic beads includes a step of moving a straw arm equipped with the washing tip and the magnetic beam together and moving the washing tip into which the magnetic beam is inserted vertically upward and downward in the sample solution containing the magnetic beads.

Preferably, the method of the present invention further includes steps of: (e) placing a remover plate having a remover hole in which a depression is formed under a straw arm equipped with a washing tip; (f) passing the straw arm equipped with the washing tip through the remover hole; (g) positioning the depression of the remover plate above an upper part of the washing tip; and (h) separating the washing tip from the straw arm by moving the straw arm to an upper part of the remover plate.

Preferably, the method of the present invention further includes steps of: (i) moving the magnetic beads from which impurities have been removed to a detection chamber; (j) placing an optical reader under the detection chamber; and (k) performing optical inspection on sample in the detection chamber by the optical reader.

Preferably, the method of the present invention further includes steps of: (l) placing a standard block over the optical reader; (m) performing optical inspection on a fluorescence measurement standard material in the standard block by the optical reader; and (n) comparing result of the optical inspection on the standard material with result of an optical inspection on a sample in the detection chamber.

Preferably, the method of the present invention further includes steps of: (o) fixing the dispensing tip to a lower part of a collection arm having a hollow penetrating vertically upward and downward inside; (p) introducing the dispensing tip into the sample solution by moving a movable body to which the collection arm is fixed; (q) collecting a sample from a sample chamber by applying suction power to the dispensing tip with a pump unit connected to a hollow of the collection arm; (r) moving the collected sample to a reaction chamber; and(s) discharging and dispensing the sample in the reaction chamber by applying discharge power to the dispensing tip with the pump unit.

Preferably, the method of the present invention further includes steps of: incubating the sample by maintaining a sample dispensed in the reaction chamber at a constant temperature.

Preferably, the method of the present invention further includes steps of: (t) dispensing a sample in a first cuvette of a plurality of cuvettes and starting incubation; (u) dispensing a sample in a second cuvette of a plurality of cuvettes and starting incubation; and (v) washing the sample in the first cuvette.

Preferably, the method of the present invention, after the step (t), further includes steps of: removing a dispensing tip used to dispense the sample in the first cuvette from the collection arm; and mounting a dispensing tip to be used to dispense the sample in the second cuvette to the collection arm; and after the step (u), further includes steps of: removing a dispensing tip used to dispense the sample in the second cuvette from the collection arm; and mounting a washing tip to be used to wash the sample in the first cuvette on the straw arm.

And, an automated liquid immunoassay device according to the present invention comprises: a straw arm capable of fixing a washing tip to a lower part and having a hollow penetrating vertically upward and downward inside; a magnetic beam positioned in a hollow of the straw arm and capable of moving vertically upward and downward; a movable body to which the straw arm is fixed; a movable body drive unit for moving the movable body; a driving motor for moving the magnetic beam; and a control unit for controlling the movable body drive unit.

Preferably, the magnetic beam is provided with a permanent magnet at a lower part thereof.

Preferably, the device of the present invention further comprises: a collection arm capable of: fixing a dispensing tip to a lower part thereof, having a hollow penetrating vertically upward and downward inside, and fixed to the movable body; and a pump unit connected to the hollow of the collection arm and capable of supplying suction power or discharge power to the dispensing tip.

Preferably, the device of the present invention further comprises a punch arm having a punch tip a lower part thereof, and fixed to the movable body; wherein length between the movable body and a lower part of the punch arm is longer than length between the movable body and a lower part of the straw arm.

Preferably, the device of the present invention further comprises a remover plate having a remover hole in which depression is formed; wherein the remover hole is larger than an area of an upper end of the washing tip.

Preferably, the device of the present invention further comprises a holder having a slot-type mount channel capable of mounting one or more cuvettes, and an inspection hole penetrating vertically upward and downward; and a holder drive unit capable of adjusting a position of the holder.

Preferably, the holder includes a heat plate for keeping a cuvette at a constant temperature at a lower part thereof.

Preferably, the device of the present invention further comprises: an optical reader having a light source, a beam splitter, lenses and a detector; and a reader drive unit capable of moving the optical reader to match an inspection hole of the holder.

Preferably, the holder includes a standard block having an optical hole penetrating in the vertical direction, and capable of mounting a fluorescence measurement standard material.

Advantageous Effects

According to the automated liquid immunofluorescence assay device according to the present invention, dispensing and reaction of the sample and reagent and purification of the reaction product through a washing module using magnetic beads are performed integrally, and it is possible to detect/read the reaction product by use of a liquid sample optical system with high sensitivity and high specificity, compared to the existing methods.

Particularly, according to the present invention, the inspection for detection, reading and analysis of the reaction product can be performed accurately and quickly under one integrated system after the sample is distributed and the reagent is reacted with the sample. So, it reduces inspection time and improves the accuracy and reproducibility of the inspection. And, it reduces the number of steps involved in the overall inspection and the cost for inspection.

In addition, the automated liquid immunoassay device according to the present invention has a holder having a plurality of mount channels so that a plurality of cuvettes are fit to one holder, and multiple diagnostics and analysis can be performed simultaneously in one system. Therefore, various inspection, diagnosis and analysis are performed quickly for accurate diagnosis in a place for examination and treatment, thereby reducing time, cost, and required manpower.

The housing included in the automated liquid immunoassay device according to the present invention can block foreign substances so as to perform more accurate sample inspection. And, it provides a drive unit for supplying vertical and horizontal movement and an optical reader on the horizontal movement path of a cuvette in leftward and rightward directions, so that sample inspection can be performed quickly and simply.

In addition, the pump unit included in the automated liquid immunoassay device according to the present invention can accurately control the amount when sample, reagent, or reaction product is inhaled or discharged through a dispensing tip.

In addition, the pulley-belt type forward and backward drive unit included in the automated liquid immunoassay device according to the present invention can prevent vibration and foreign substances caused by friction made by leftward and rightward movement, so that more accurate inspection can be made, unlike the gear type.

In addition, the arm unit provided in the automated liquid immunofluorescence assay device according to an embodiment of the present invention is provided with a punch arm, a collection arm and a straw arm, so that they are integrated into an all-in-one module. Therefore, when dispensing a pump, driving a puncher, washing, and separating a dispensing tip from a washing tip, it is possible to control the positions of them vertically upward and downward with one driving motor. Therefore, unlike when each module is configured to be controlled by each driving motor separately, it is possible to reduce the size and the production cost.

In addition, in the device according to the present invention, when a plurality of cuvettes are used, a set of dispensing tips and washing tips can be used without having to replace the tip in the middle of the reaction for each cuvette, and the tip can be easily removed by a remover module.

In addition, the device according to the present invention includes a standard block so that the variation of signal values of devices can be reduced.

DESCRIPTION OF DRAWINGS

FIG. 18 is a flowchart showing the washing process in the automated liquid immunoassay method according to an embodiment of the present invention.

BEST MODE

Figure 1:
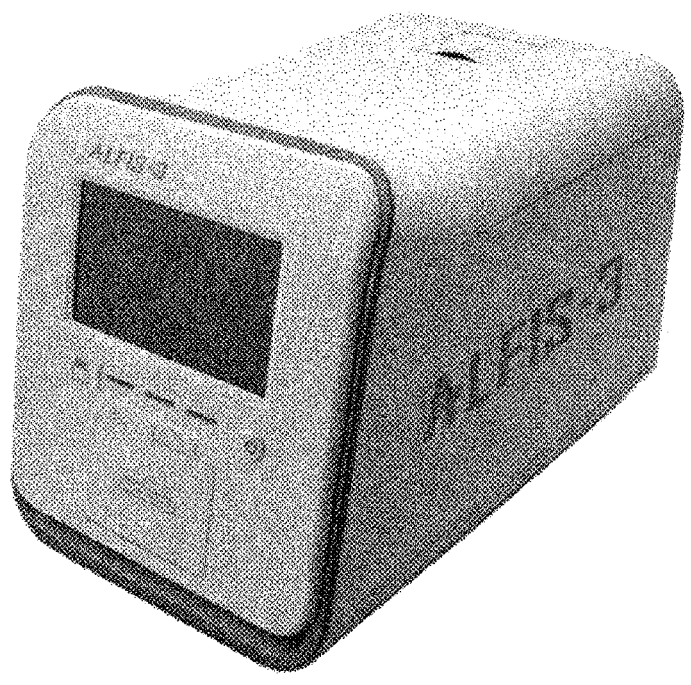
FIG. 1 is a photograph of the appearance of the device actually manufactured according to an embodiment of the present invention.

Hereinafter, exemplary embodiments of the present invention will be described with reference to the accompanying drawings. These embodiments are illustrative and do not limit the present invention in any way.

The spatially relative terms such as "downward", "backward", "forward" and "upward" can be used in order to easily describe the correlation of one element or component with another elements or components, as shown in drawings. Spatially relative terms are to be understood as terms that include different directions of the device in use or operation in addition to the directions shown in the drawings. For example, when an element shown in the drawings is turned upside down, the element described as "below" or "under" another element is supposed to be thought actually placed "above" another element. So, the exemplary terms such as "below" can encompass both orientations of "above" and "below." The element can be oriented in other directions, and thus spatially relative terms may be interpreted according to the orientation. For instance, the terms "horizontally leftward and rightward" may also be interpreted as "vertically upward and downward" and they are not limited by their dictionary meanings.

In this specification, the spatially relative terms herein refer to the orientation when looking at the front of the device according to the present invention.

In the present specification, the angle and the direction mentioned in describing the structure of the present invention are based on those depicted in the drawings. In this description, if the reference point with respect to an angle and the positional relationship are not clearly mentioned in description of the structure constituting the present invention, the relevant drawings are referenced.

Hereinafter, most of all, the terms used in the present specification and the principles of chemical reactions used with the device will be described.

In the present specification, "detection" is used to mean analyzing quantitatively or qualitatively the analyte contained in sample by purifying the reaction product after the reaction between the reagent and the sample in order to determine the presence or the amount of the analyte contained in the sample. The detection result is read by an automated liquid immunoassay device 1 according to an embodiment of the present invention.

In this specification, the term "inspection" is used as a term encompassing all of detection, analysis and reading.

The term "sample" used in this specification refers to a composition that is expected to include an analyte, and a sample that can be used in the present invention is a liquid material or a fluid material similar to liquid. The sample used in an embodiment of the present invention is a biological sample, and can be a biological body-derived body component such as whole blood, plasma, serum, urine, saliva, manure and cell extracts.

The term "analyte" used in this specification refers to an analytical compound in a sample, also referred to as a target or indicator, including but not limited to a protein component such as an antigen and a nucleic acid material such as gene.

In this specification, "reagent" is substance used in admixture with a sample for quantitative or qualitative analysis of an analyte contained in a sample, and varies according to a specific analyte. It may include but is not limited to, for example, a reaction buffer, a dilution buffer, a detection buffer, a wash buffer or various substances in the sample such as enzymes, substrates or certain antibodies that react with antigens for instance.

FIG. 1 shows the appearance of the device 1 manufactured according to an embodiment of the present invention.

Figure 2:
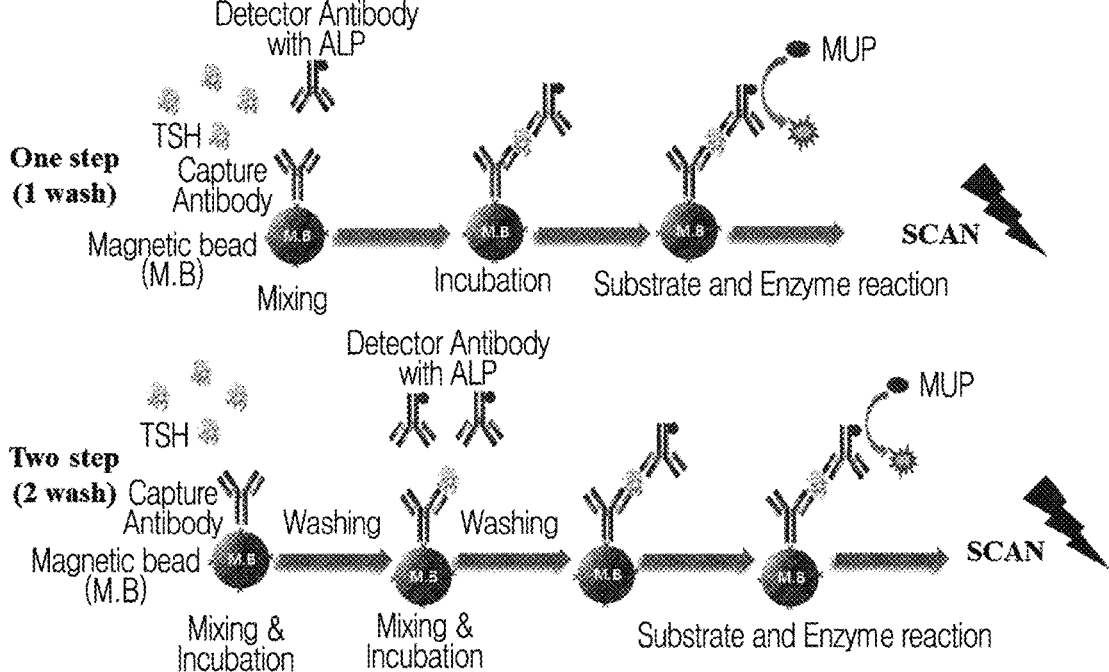
FIG. 2 is a schematic diagram illustrating the process of the sandwich immunoassay using the magnetic beads used in the device according to an embodiment of the present invention.
Figure 3:
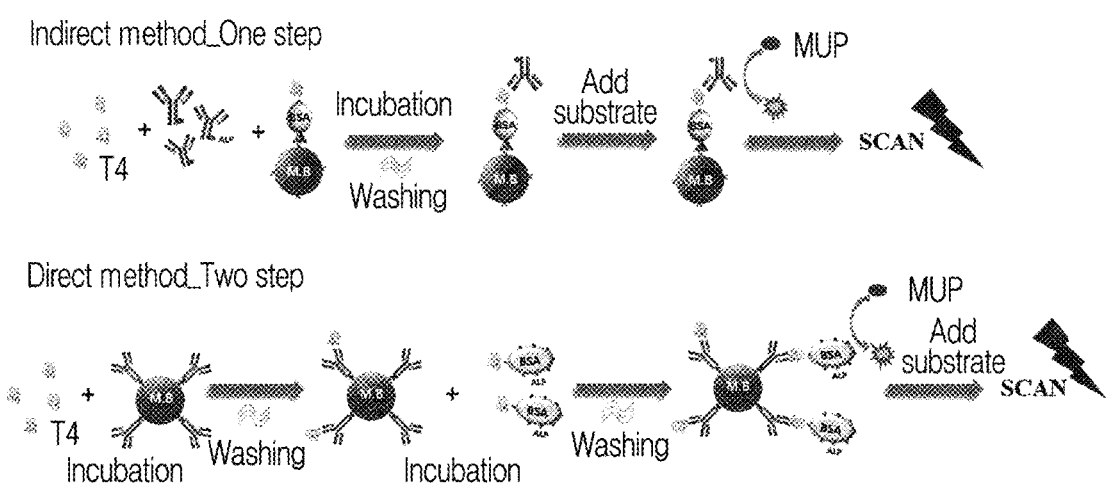
FIG. 3. is a schematic diagram illustrating the process of the competition immunoassay using the magnetic beads used in the device according to an embodiment of the present invention.

The automated liquid immunoassay device 1 according to an embodiment of the present invention is a device optimized for the immunoassay (ELISA)-based reaction based on the specific binding between antigen and antibody, the detection of certain component or analyte contained in biological sample through the reaction as shown in FIGS. 2 and 3 for example, and the physical washing to space the unreacted substance apart from reaction product by using magnetic beads before detecting analyte.

FIGS. 2 and 3 illustrate various ELISA analysis process for analyzing analyte. Sandwich immunoassay refers to a type of immunoassay in which a capture antibody and a detector antibody are bonded to each other in the form of sandwich, and the detector antibody is chemically bonded with an enzyme so as to induce a quantitative reaction with a substrate. At this time, used is the conjugate in which capture antibody is chemically or physically bonded to the magnetic beads and the detector antibody is bonded to the enzyme. Depending on how many steps in which the washing is performed, the sandwich immunoassay using the magnetic beads can be categorized into two types: one-step assay and two-step assay. The two-step assay is performed as follows: the sample is first reacted with and the capture antibody, washed, and then lastly reacted with the detector antibody. The one-step assay is as follows: the sample is reacted with the capture antibody and the detector antibody at the same time (FIG. 2).

The competition assay which is widely used to detect small amounts of protein molecules besides the sandwich immunoassay is also categorized into two types: indirect competition assay and direct competition depending on whether competition proteins or antibodies are conjugated to the magnetic beads. And it can be also categorized into one-step assay and two-step assay according to how many steps the immunoassay is performed in. For example, FIG. 3 illustrates an example of indirect competition immunoassay and an example of direct competition immunoassay among competition assays.

In one embodiment of the present invention, a fluorescence signal is used for detection of the reaction product. In this case, used is enzyme-substrate reactions such as alkaline phosphatase (ALP) and 4-methylumbelliferyl phosphate (MUP). ALP, a type of enzyme, is a representative enzyme that causes dephosphorylation. 4-MUP is reacted with ALP, and dephosphorylation takes place irreversibly by enzymatic hydrolysis. The resulting 4-MU (4-Methylumbelliferone) is excited at 360 nm wavelength and emits fluorescent light with 450 nm wavelength. The concentration of the analyte in the sample is determined by detecting this fluorescence signal intensity.

In another embodiment of the present invention, colorimetric methods are used for detection of the reaction product. Color change analysis is detecting changes in the visible color of a particular visible light wavelength at which the reaction product absorbs light. The signal of the reaction product is used to determine the concentration of the analyte in the sample by detection of the absorbance. Examples of the representative enzymes and substrates are peroxidase, its substrates TMB (3,3',5,5' tetramethylbenzidine), DAB (3,3', 4,4' diaminobenzidine) and 4CN(4-chloro-1-naphthol), ABTS (2,2'-azinodi[3-ethyl-benzthiazoline] sulfonate, and OPD (o-phenylenediamine). However, the present invention is not limited to the examples listed above. For example, in the case of using TMB as a substrate, blue color is generated, which can be detected with the light of 650 nm wavelength. In the case of using ABTS, turquoise color is generated, which can be detected with the light in the range of 405 nm to 410 nm wavelengths. Another examples of an enzyme substrate are ALP, its substrate BCIP/NBT (5-bromo-4-chloro-3-indolylphosphate/nitroblue tetrazolium) and p-NPP (p-nitro-phenylphosphate). However, the present invention is not limited to the examples listed above, which generate dark yellow color and can be detected with the light in the range of 405 nm to 410 nm wavelengths.

In another embodiment of the present invention, chemiluminescence is used for detection of the reaction product. Chemiluminescence refers that the excitation electrons generated by chemical reaction return to the ground state resulting in emitting light. No light source is required and it is measured in RLU (relative light units) per hour and used to determine the concentration of analyte in the sample. Examples of enzymes and substrates are peroxidases and its substrates such as luminol, polyphenols (including pyrogallol, perperogallin, gallic acid and umbeliferon for example) and acridine esters or luciferin (in case of this, referred to as bioluminescence), but these examples does not limit the present invention. Other examples of enzymes and substrates are ALP and AMPPD (3-(2'-spiroadamantyl)-4-methoxy-4-(3"-phosphoryloxy)-phenyl-1,2-dioxetane). However, they do not limit the present invention.

Such assays require particularly high sensitivity detection of high specificity, which requires removal of non-specific or unreacted materials. In other words, in the inspection process, it is requires to purify the reaction product for accurate detection of the reaction product after the reaction of the reagent and the sample. The device according to the present invention is optimized for effective removal of such unreacted material.

Specifically, the device according to an embodiment of the present invention is optimized to remove the non-reactant by the physical wash using magnetism, separate only the product of the specific reaction in the form of magnetic beads using a permanent magnet, concentrate it, selectively bond an enzyme-attached detector to the reaction product and finally react the enzyme with a substrate so as to detect a signal from the reaction product.

The reaction used in the device according to one embodiment of the present invention is carried out in a liquid state in a cuvette mounted on the device. The device according to an embodiment of the present invention is optimized for the performance of the reaction steps optimized in consideration of the characteristics of the various parameters involved in the reaction for the performance of the reaction in the cuvette and the detection of the reaction product.

Most of all, the cuvette 10 used in the automated liquid immunoassay device 1 according to an embodiment of the present invention will be described.

Figure 4:
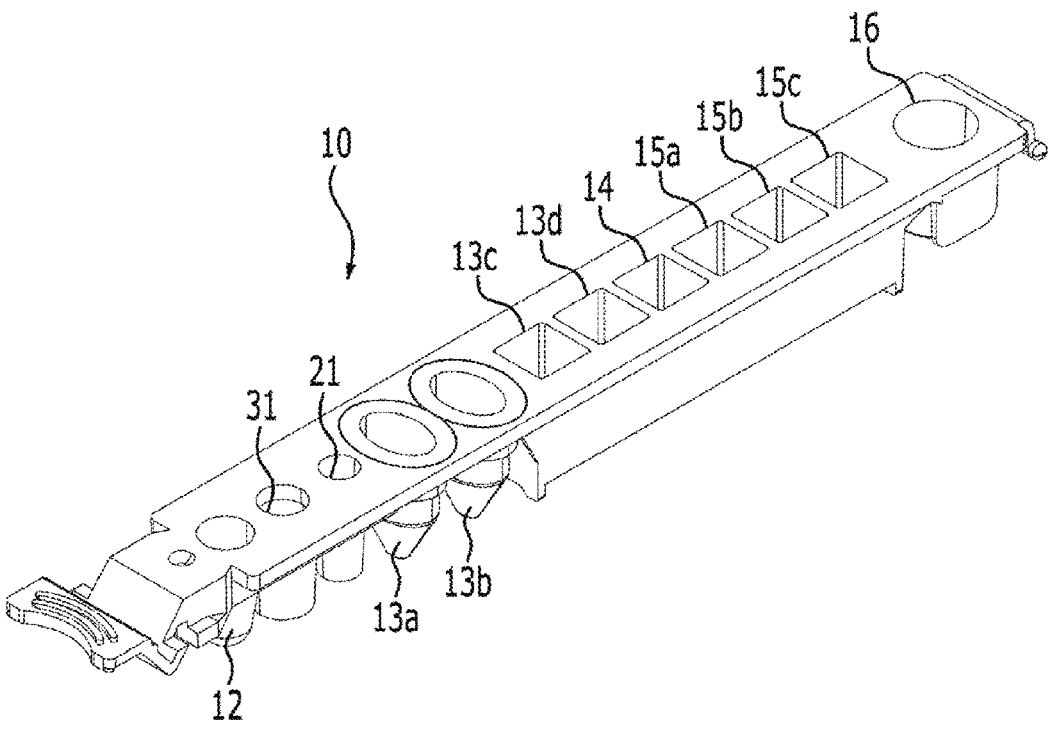
FIG. 4 shows the structure of a cuvette used in the device according to an embodiment of the present invention.
Figure 5:
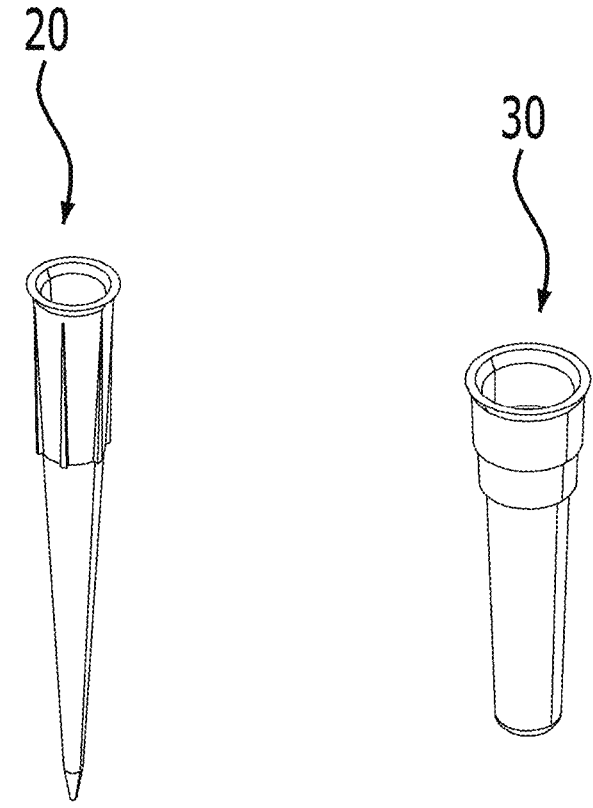
FIG. 5 shows the dispensing tip and the washing tip used in conjunction with the cuvette used in the device according to an embodiment of the present invention, respectively.
Figure 6:
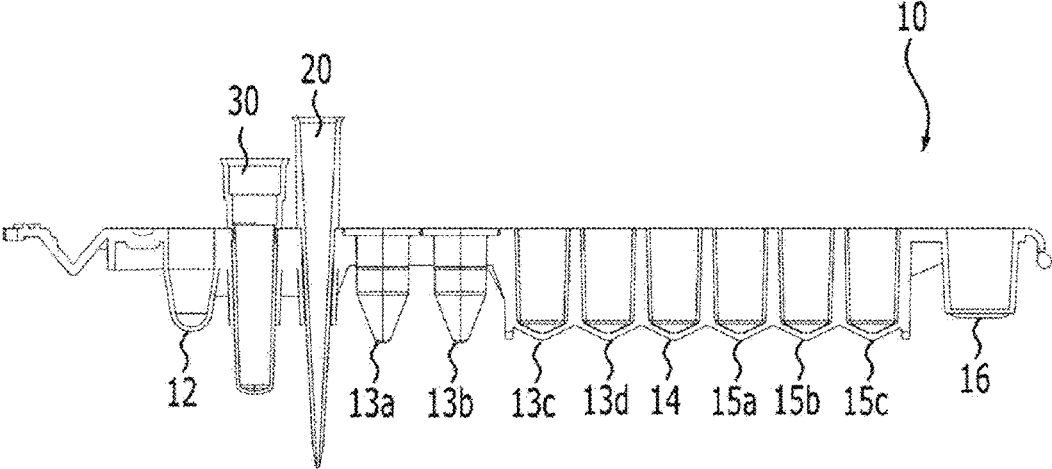
FIG. 6 shows a form of a cuvette equipped with a dispensing tip and a washing tip used in the device according to an embodiment of the present invention.

FIG. 4 shows the structure of a cuvette 10 used in the device according to an embodiment of the present invention. FIG. 5 shows the dispensing tip 20 and the washing tip 30 used in the device according to an embodiment of the present invention, respectively. FIG. 6 shows a form of a cuvette 10 equipped with a dispensing tip 20 and a washing tip 30 used in the device according to an embodiment of the present invention.

The cuvette 10 used in the automated liquid immunoassay device 1 according to an embodiment of the present invention is used for reaction for detecting an analyte contained in a sample. In cuvette, the reaction of reagent with sample is carried out so as that the reaction product is generated and then washed.

The cuvette 10 used in the automated liquid immunoassay device 1 according to an embodiment of the present invention may have a long shape extending in the forward and backward directions, as shown in FIGS. 4 and 6. In addition, the cuvette 10 may include one or more than one fitting holes and a plurality of chambers. Such chambers may also be referred to as wells.

The fitting hole is a place where the washing tip 30 and the dispensing tip 20 as described in FIG. 5 are inserted and waits until the inspection starts or during the inspection process, and the washing tip fitting hole 21 and the dispensing tip fitting hole 31 are provided, respectively.

The chambers may include a sample filling chamber 12, buffer and dilution chambers 13a, 13b, 13c and 13d, a reaction chamber 14, a washing chambers 15, and a detection chamber 16 in order.

Alternatively, as shown in FIGS. 4 and 6, the chambers may include the sample filling chamber 12, a washing tip fitting hole 21 and a dispensing tip fitting hole 31, a buffer and dilution chambers 13a, 13b, 13c, and 13d, the reaction chamber 14, the washing chambers 15, and the detection chamber 16 in order.

In addition, the chambers may be sealed by a to prevent predetermined sealing film (not shown) denaturation or contamination of reagents.

The sample filling chamber 12 is provided to fill various samples such as biological samples to be analyzed. As described above. The sample filling chamber 12 can be formed on the front or rear of the washing tip fitting hole 21 and the dispensing tip fitting hole 31.

The buffer and the dilution chambers 13a, 13b, 13c and 13d are filled with magnetic beads (MB) buffers necessary for the reaction, detection buffers and sample dilution buffers. The sample filling chamber 12 or the washing tip fitting hole 21 and the dispensing tip fitting hole 31 are provided in the above-mentioned order so as to dilute the sample.

The reaction chamber 14 is provided to react the sample with the reagent and is formed at the rear of the buffer and dilution chamber.

A plurality of the washing chambers 15 may be provided, in which a reaction product can be washed after the reaction in the reaction chamber. In one embodiment of the present invention, the three washing chambers 15a, 15b, and 15c are provided.

The detection chamber 16 is the place where detected is the reaction product generated by the reaction of the sample with the reagent, which is provided to detect the analyte in the reaction product after the washing in the washing chamber 15. The detection chamber 16 is formed at the rear of the washing chamber 15, and may be configured to have a light transmittance for detecting a fluorescent signal.

In one embodiment of the present invention, the cuvette 10 may further include a barcode or a QR code (not shown), which interworks a below-described chip inserted into an automated liquid immunoassay device 1 according to the present invention. In the present invention, the barcode includes, but is not limited to, UPC-A, UPC-E, EAN, Code 3 of 9, Interleaved 2 of 5, Code 128, UCC/EAN-128, Codabar, PostNet, Pharmacode, or PDF-417. Alternatively, the barcode includes, but is not limited to, 1D barcodes or 2D barcodes. The barcode and the QR code show a type of analyte according to the type of sample.

The cuvette 10 used in the automated liquid immunoassay device 1 according to an embodiment of the present invention is equipped with a dispensing tip 20 and a washing tip 30.

Dispensing tip 20 may include a disposable microtip (e.g. a micropipette tip of 2-1000 μl volume) which is engaged with a below-described collection arm 556 for dispensing the sample and/or reagents to the chambers described above, in other words, from one chamber into another chamber. The dispensing tip 20 has a tubular shape. The diameter of the dispensing tip 20 may gradually decrease toward its end, so that its end part may have a pointed shape.

Dispensing tip 20 described above can be used with equipment that does not have a separate reagent supply device and a means for washing the contamination, so that the operation of the equipment may be simplified.

The plurality of cuvettes used in the device according to an embodiment of the present invention are configured to be equipped with a dispensing tip and a washing tip for each cuvette. The tips used in one cuvette can be used separately from the tips used in other cuvettes, so as to prevent contamination. The automated equipment using a conventional metal needle should be equipped with a washing device in order to prevent contamination. Consequently, the volume of the equipment is increased because of the additional device, and the additional washing process is necessary so that there is a problem that the inspection cost increases.

In particular, the dispensing tip 20 is fitted into the dispensing tip fitting hole 21 of the cuvette 10. When the inspection process starts, the dispensing tip 20 is fastened to a collection arm 556 which will be described below, and inhale or discharge the sample or the reagents so as to distributing or dispensing them to the chambers together with the pump unit 506. In addition, during the inspection process, the dispensing tip used in the first cuvette may be temporarily stored in the fitting hole 21 for the reaction in the second or third cuvette while the reaction occurs in the first cuvette. Therefore, only one tip is needed to use in one cuvette without changing the tip in the middle until the inspection is finished, so that it is convenient and the reaction time may be reduced. This is explained in more detail in the description of the operation of the device according to one embodiment of the invention.

The washing tip 30 has predetermined height, predetermined width and a tubular shape, and its lower end is sealed. A injection hole having predetermined depth and predetermined inner diameter is formed at an upper part of the washing tip 30. The washing tip 30 is made of a non-magnetic material to transfer the magnetism, and may be made of a flexible material to facilitate fixing to the washing arm and detaching from the washing arm. The washing tip 30 is also seated in the washing tip fitting hole 21 of the cuvette 10. When the inspection process starts, the washing tip 30 is fastened to the straw arm 554 to perform washing as described below. In addition, during the inspection process, the washing tip used in the first cuvette may be stored in the fitting hole 31 for the reaction in the second or third cuvette while the reaction occurs in the first cuvette. Therefore, only one tip is needed to use in one cuvette, so that it is convenient and the reaction time may be reduced. This is explained in more detail in the description of the operation of the device according to one embodiment of the invention.

Three cuvettes according to one embodiment of the present invention are used, and are optimized for three types of analysis. There are, for example, three different analytes in the same biological sample such as FT4 (Free Thyroxine) for thyroid diagnosis, TSH (Thyroid Stimulating Hormone) and T3 (triiodothyronine). And For example, hCG (chorionic gonadotropin) for examination of birth defects, E3 (Estriol) and AFP (Alpha Feto Protein) can be listed.

Hereinafter, an automated liquid immunoassay device 1 according to an embodiment of the present invention will be described.

Figure 7:
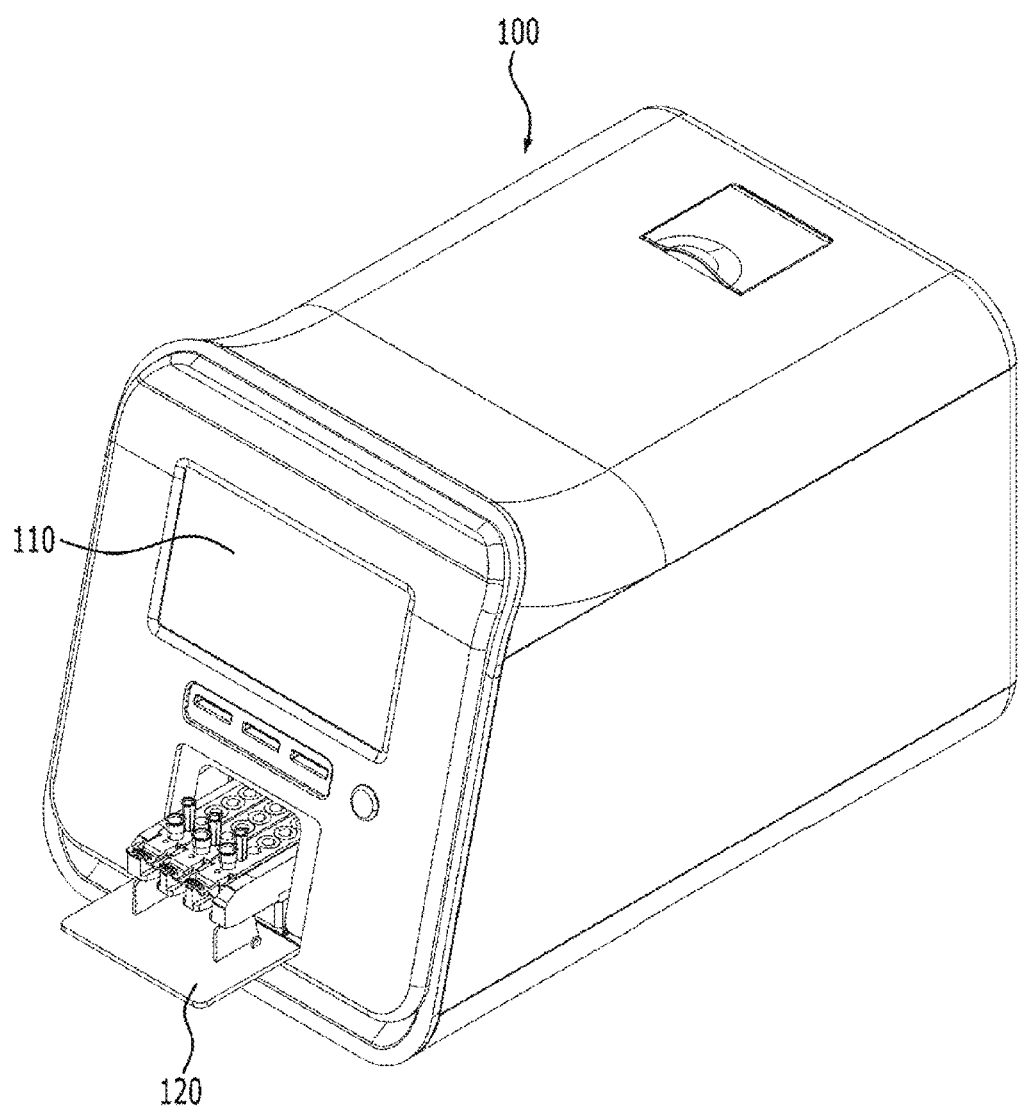
FIG. 7 shows the appearance of the device according to an embodiment of the present invention.
Figure 8:
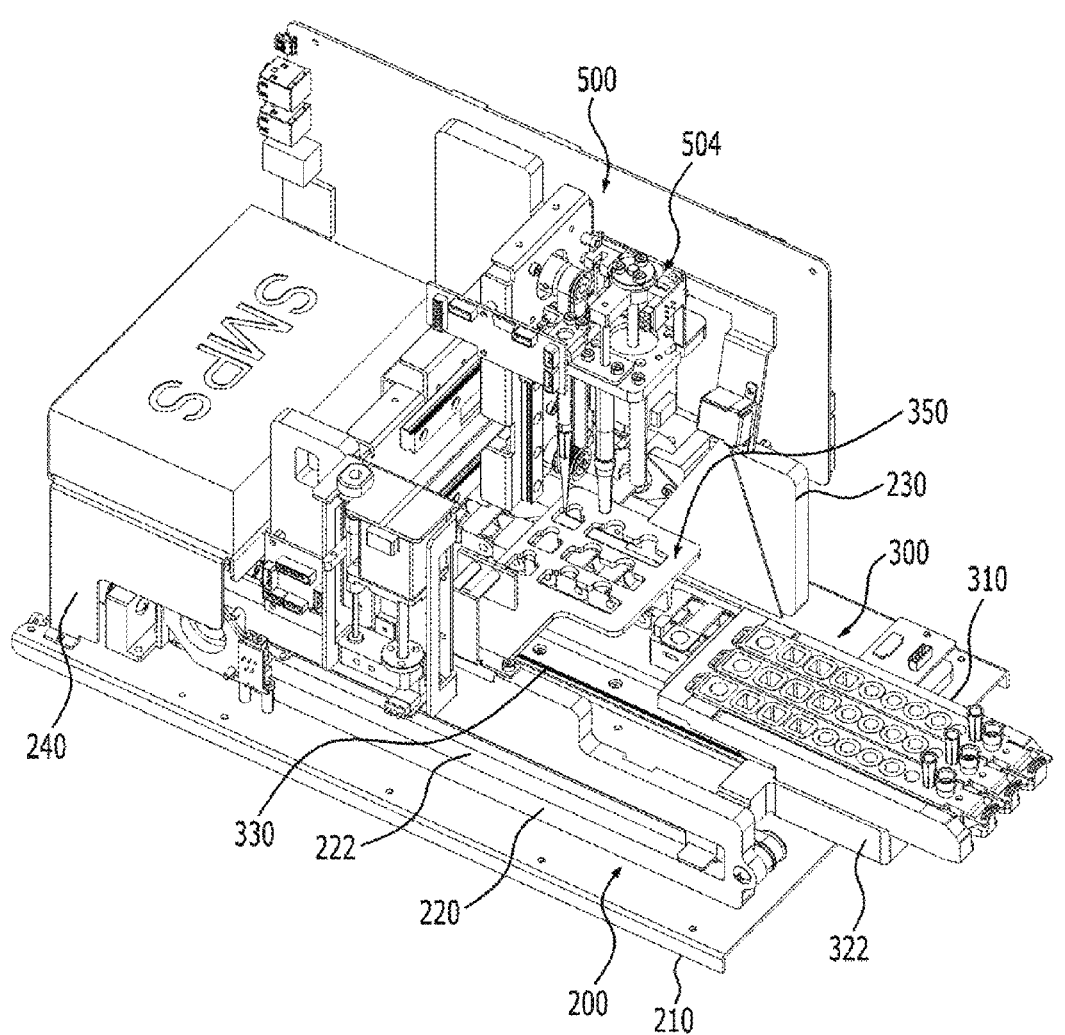
FIGS. 8 and 9 show the device without its housing according to an embodiment of the present invention.
Figure 9:
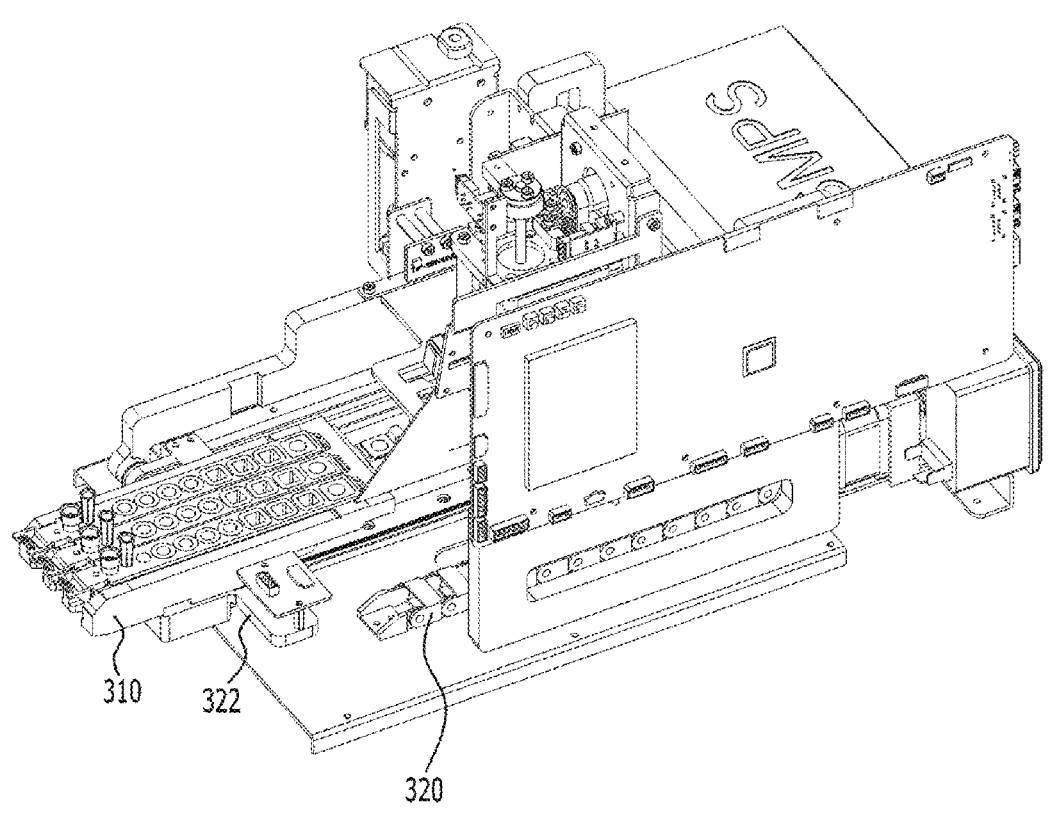

FIG. 7 shows the appearance of the device 1 according to an embodiment of the present invention. FIGS. 8 and 9 show the device without its housing 100 according to an embodiment of the present invention, from different angles respectively.

The automated liquid immunoassay device 1 according to an embodiment of the present invention is for inserting a cuvette 10 and inspecting a sample. It can include a housing 100, a frame 200, a cuvette module 300, an optical reading module 400 and a dispenser module 500.

The housing 100 forms the entire exterior of the automated liquid immunoassay device 1, and blocks the foreign substances from flowing into the inside.

The housing 100 includes various input units for manipulation and a display unit 110 for output. In addition, the housing 100 is equipped with an inlet and outlet 120 into which the cuvette 10 is inserted. When the cuvette 10 enters the inside of the housing 100 through the inlet and outlet 120, the foreign substances are blocked from entering the chamber in the cuvette 10 through the housing 100, so that the more accurate sample inspection is possible.

The frame 200 is provided in the housing 100 to fix a cuvette module 300, an optical reading module 400 and a dispenser module 500. The frame 200 may include a lower frame 210, a first side frame 220, a second side frame 230, and a rear frame 240.

The lower frame 210 is seated at the lower part of the automated liquid immunoassay device 1. The lower frame 210 may have a plate shape having a predetermined area.

The first side frame 220 and the second side frame 230 are disposed on the left side and the right side of the lower frame 210, respectively, and may be stood with a predetermined height. In addition, the first side frame 220 and the second side frame 230 may have guide spaces 222 and 232 for guiding the forward and backward displacement of a holder 310, respectively.

The rear frame 240 is positioned at the rear of the device, and may be provided so as to fix a predetermined control device or the like.

Figure 10A:
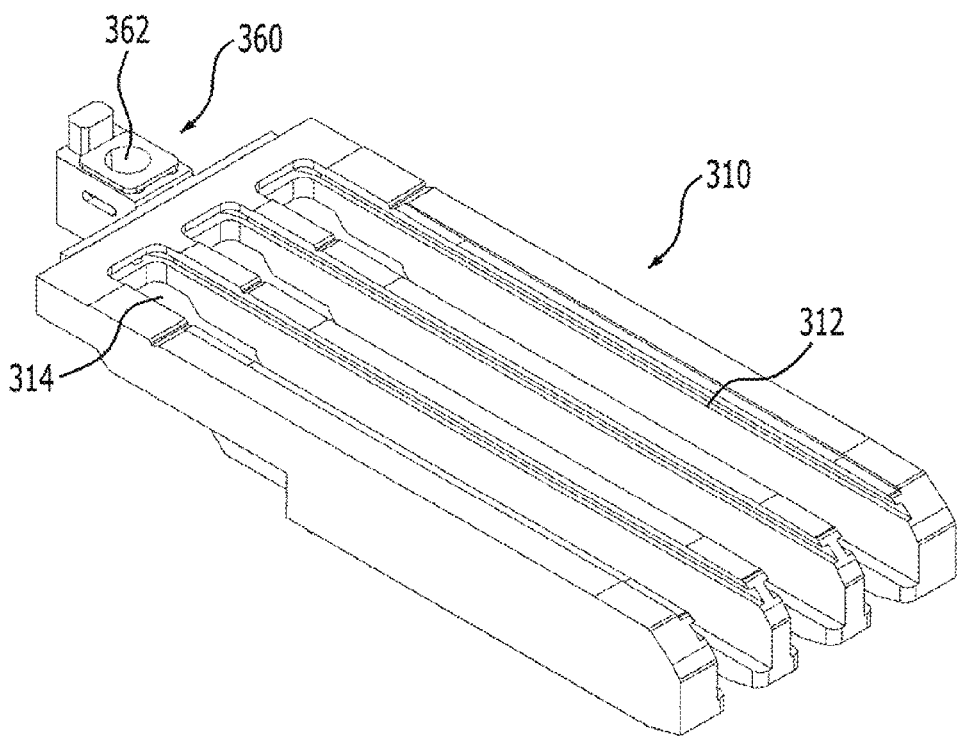
FIGS. 10 and 11 show a holder of the device according to an embodiment of the present invention and the cuvettes mounted on the holder, respectively.
Figure 10B:
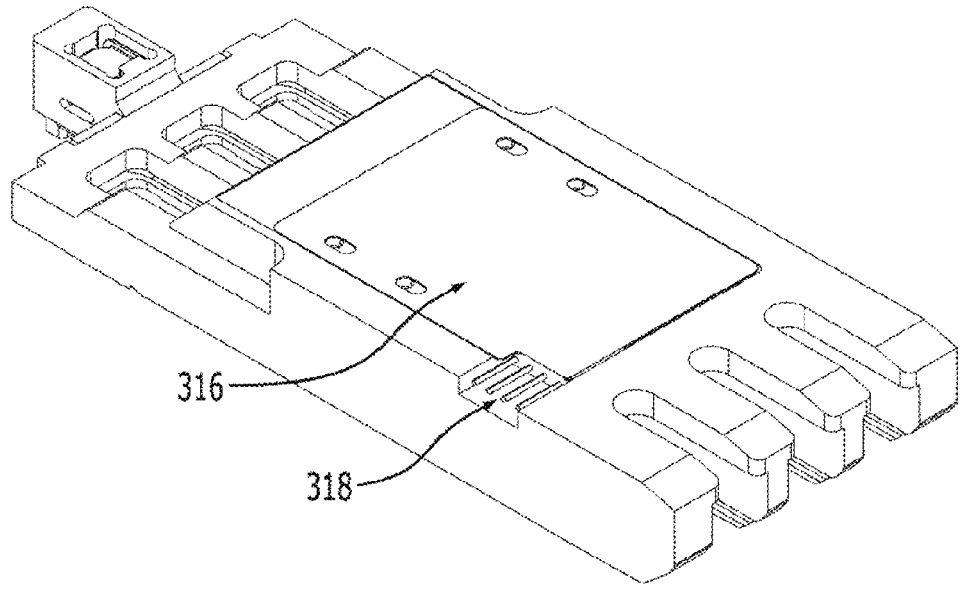
Figure 11:
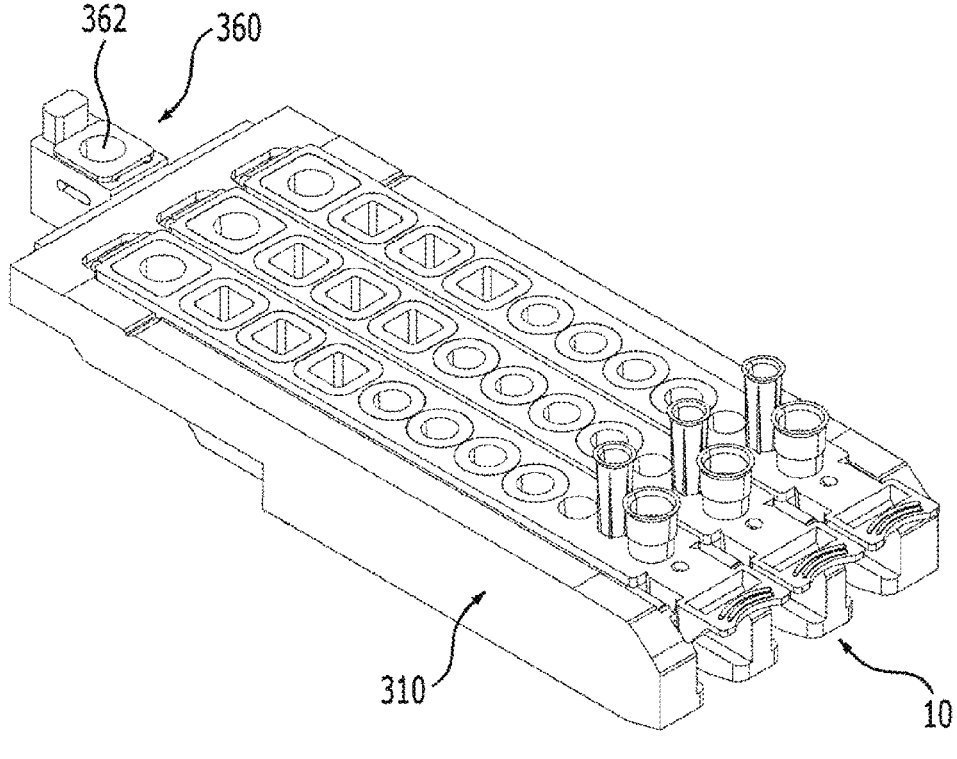
Figure 12:
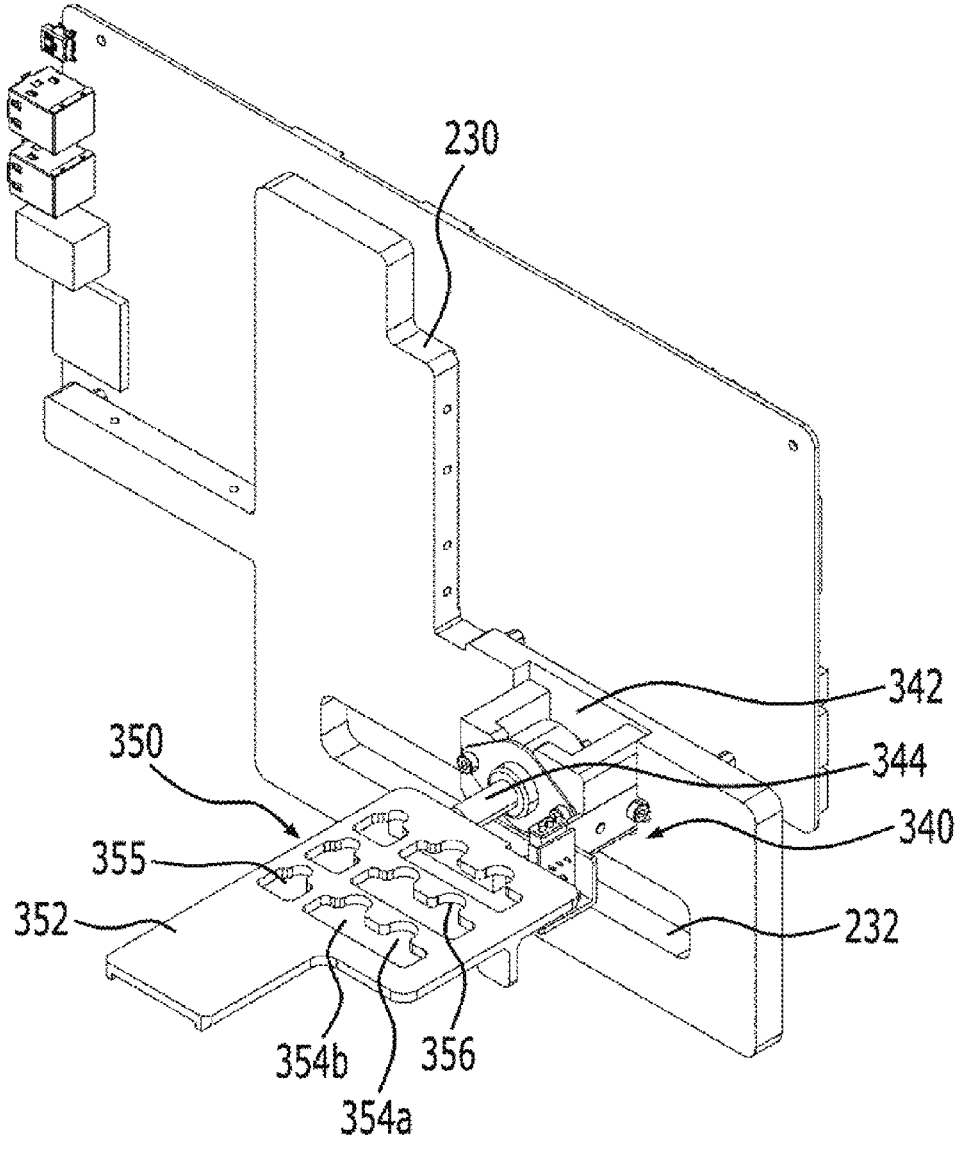
FIG. 12 shows the structure of a remover module of the device according to an embodiment of the present invention.
Figure 13:
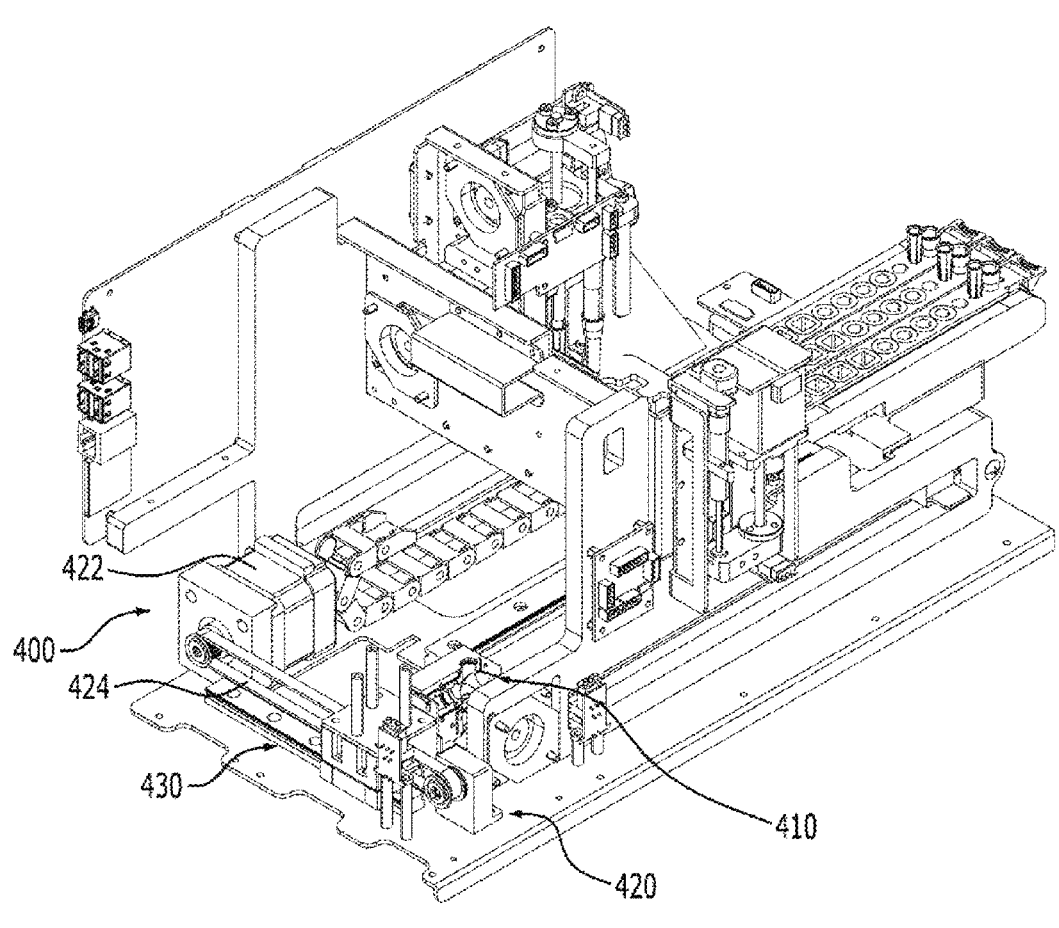
FIG. 13 is a rear view of the inside of the device according to an embodiment of the present invention.

FIGS. 10a, 10b and 11 show the holder 310 of the automated liquid immunoassay device according to an embodiment of the present invention and the cuvettes mounted on the holder 310, respectively. FIG. 12 shows the structure of a remover module 340 of the automated liquid immunoassay device according to an embodiment of the present invention. FIG. 13 is a rear view of the inside of the automated liquid immunoassay device according to an embodiment of the present invention.

The cuvette module 300 will be described below.

The cuvette module 300 is provided in the housing 100 and is a device for accommodating the cuvette 10 and moving the cuvette 10 forward and backward.

The cuvette module 300 may include a holder 310, a holder drive unit 320, a holder guide unit 330, and a remover module 340.

Holder 310 is a member on which the cuvette 10 can be seated. For example, the holder 310 may be disposed on the lower frame 210 but behind the inlet and outlet 120 of the housing 100. Therefore, the cuvette 10 can be pushed into the holder 310 through the inlet and outlet 120.

On the other hand, the holder 310 may have a mount channel 312 in the form of a slot so that the one or more cuvettes 10 may be inserted and mounted. The mount channel 312 may be extended in the forward and backward directions and open forward.

An inspection hole 314 is formed at the rear end of the mount channel 312. The inspection hole 314 is configured to penetrate in the vertical direction. Therefore, when the cuvette 10 is accommodated and mounted on the mount channel 312 of the holder 310, the lower part of the some rear part of the holder 310 is exposed downward through the inspection hole 314. Specifically, the lower part of the detection chamber 16 disposed behind the cuvette 10 may be exposed downward through the inspection hole 314.

In addition, a plurality of mount channels 312 may be formed in the holder 310 such that a cuvette 10 may be inserted into each of the mount channels 312 and a plurality of cuvettes 10 can be inspected. In this case, a plurality of the mount channels 312 may be arranged side by side in parallel to each other in one holder 310.

The lower part of the holder 310 includes a heat plate 316 and a heat plate power supply 318. This is to automatically control to keep the cuvette and the reactants contained in the cuvette at a constant temperature during the reaction, which ensures the precision and accuracy of the on inspection, depending the characteristics of the biological sample sensitive to temperature.

A heat plate 316 heats the holder 310 to heat to a constant temperature or maintain at a specific temperature the cuvette 10 and the samples and the reactants contained in the cuvette by convection. The temperature is automatically controlled by an embedded program. A temperature sensor is adopted for automatic control. In an embodiment of the invention, the temperature sensor is used inside the holder, the heat plate and the device. The temperature sensor of the device is used to control the temperature inside the device because the temperature inside the device affects the optical system. The temperature sensor of the heat plate is used to control the temperature of the heat plate, and the temperature sensor of the holder measures the temperature of the holder to control the heat plate in a feedback manner.

The holder drive unit 320 can adjust the position of the holder. In one embodiment of the present invention, the holder drive unit 320 may include members that apply a force to the holder in the forward and backward directions. The holder drive unit 320 may include a movable body 322 to which the holder 310 is fixed, a driving motor, and a predetermined transmission member that transmits the power of the driving motor to the movable body 322. A servo motor, a step motor, a DC motor, etc. can be used as the driving motor.

The holder guide unit 330 is provided to guide the displacement of the holder 310 in the forward and backward directions. The holder guide unit 330 may include a predetermined guide rail extending in the forward and backward directions and a predetermined guide unit that is connected to the guide rail, movable along the guide rail forward and backward and connected to the movable body 322.

The remover module 340 is used for dispensing/mixing reagents in different cuvettes during the immune response time (incubation), and for removing the tips after reaction completion in each cuvette, after the use of the dispensing tip and the washing tip in an immunological inspection.

The remover module 340 includes a predetermined drive device 342 that can be fixed to the second side frame 230, and a predetermined remover plate 350 that can be displaced by the drive device 342. The drive device 342 and the remover plate 350 may be connected through a predetermined shaft 344.

The remover plate 350 is positioned between a holder 310 and a dispenser module 500 as shown in FIG. 8. Referring to FIG. 12, the remover plate 350 has a plate body 352. In the plate body 352, formed is a remover line in which three remover holes 354a, 354b, and 355 are formed in series. The remover lines are formed as many as mount channels 312 formed in the holder 310. The two remover holes 354a and 354b on the remover line are formed to be connected to each other, and are positioned between the holder 310 and the dispenser module 500. A punch arm 552 and a straw arm 554 described later respectively pass through the remover holes. The collection arm 556 passes through one remover hole 355 formed solely on the remover line.

Each remover hole 354a, 354b, 355 may have a depression part 356 recessed to one side. Therefore, the dispensing tip 20 interlocked on the collection arm 556 and the washing tip 30 interlocked on the straw arm 554 are positioned in the corresponding remover holes 354a, 354b, 355. A remover plate 350 is displaced in the left horizontal direction so that the collection arm 556 is positioned in the depression part 356. Then the upper part of the dispensing tip 20 is positioned partly below the depression part of the plate. If the collection arm or the straw arm moves upward, a force is applied to the dispensing tip 20 interlocked with the collection arm 556 or the upper part of the washing tip 30 interlocked with the straw arm 554, so that the tips can be removed from the arms.

The remover hole 355 is bigger than the areas of the upper ends of the dispensing tip 20 and the washing tip 30, so that the collection arm equipped with the dispensing tip or the straw arm equipped with the washing tip can pass through the remover hole. It is desirable that the collection arm or the straw arm can be seated in the depression part since the depression part 356 is larger than the radius of the collection arm or the straw arm. It is preferable that the depression part 356 is formed smaller than the area of the top of the dispensing tip or the washing tip so that the top of the dispensing tip or the washing tip can be caught in the protruding part. However, the shape of the depression part does not matter a lot if the dispensing tip or the washing tip is spaced apart from the collection arm or straw arm.

The reaction occurring in the cuvette 10 used in the device according to an embodiment of the present invention requires at least two incubation processes from start to detection. As the device according to an embodiment of the present invention is provided with a remover module 340, only one dispensing tip and one washing tip are used in one cuvette as described below, and reaction in other cuvettes mounted on other mount channels 312 can be ready during incubation time.

Specifically, during the first incubation time for the immune response to occur in the cuvette mounted on the first mount channel 312, in order to dispense/mix reagent in the cuvette provided in the second mount channel, the dispensing tip 20 and the washing tip 30 having been used in the first channel are temporarily stored in the corresponding parts 21 and 32 of the first cuvette, and the temporarily stored dispensing tip 20 and washing tip 30 can be reused after the first incubation time elapses. That is, in case that no remover module 340 was provided, the dispensing tip 20 and the washing tip 30 once used in the first mount channel cannot be used again but are discarded. And then, the next processes should take place with new installation of the tips after the first incubation time elapses. So, at least two dispensing tips 20 and at least two washing tips 30 are required for each cuvette mounted on the mount channel. However, the present invention provides the remover module 340 so that the inspection process can be performed with only one dispensing tip 20 and one washing tip 30 for each cuvette.

The device according to an embodiment of the present invention may include a standard block 360. The standard block 360 is fixed to the holder 310 so to be displaced together with the holder 310 and may be positioned behind the holder 310. Preferably, the standard block 360 may be positioned behind at least one of the inspection holes 314.

The standard block 360 has a predetermined optical hole 362 penetrating vertically, and the optical hole 362 may provided with a predetermined optical means that can be optically detected or captured.

In one embodiment of the invention, the standard block 360 comprises an optical means. In one embodiment of the present invention, the optical means included in the standard block 360 mounts a fluorescence measurement standard material having a predetermined fluorescence value. A material having appropriate excitation and emission wavelengths may be used as a fluorescence measurement standard material according to the type of fluorescence detected in the reaction product. In an embodiment of the present invention, 4-Methylumbelliferone sodium salt having an excitation wavelength of 360 nm and an emission wavelength of 450 nm is used, but the present invention is not limited thereto.

In another embodiment of the present invention, the optical means included in the standard block 360 is equipped with a visible color absorbance measurement standard material. The absorbance measurement standard material may be properly selected according to the absorbance area of the visible color detected in the reaction product. In one embodiment of the present invention, a glass plate, a plastic plate, a gel, an appropriate liquid solution, etc. are used, but the present invention is not limited thereto.

When the fluorescence or absorbance value of the reaction product is measured after completion of the reaction in the optical analysis, the standard fluorescence or absorbance mounted on the standard block 360 is first scanned and the signal value of the reaction result is measured so as to display them as a ratio. In order to eliminate the deviation of devices, the ratios of the measured value of the instruments to that of a standard stance are calculated and compared with the data embedded as the master calibration graph so as to accurately calculate the concentration of the analyte in the sample.

In case of measuring fluorescence or an absorbance signal, the absolute values of the fluorescence values of devices are usually different. Therefore, when the concentration is calculated using the absolute value of fluorescence, there may be an error due to a device. Therefore, in one embodiment of the present invention, if a ratio of a measured value to that of a standard material of a standard block is used, the errors in measured values of devices are reduced and accuracy and reproducibility are improved.

The device according to another embodiment of the present invention may exclude the standard block 360, but even if it includes the standard block 360, the standard block may be decided not to use. For example, if the signal detected in the reaction product is determined to be chemiluminescence, the standard block may be excluded, or even if the standard block is included, the standard block may be decided not to use. In this case, the device includes a photo detector such as a PMT and an avalanche photodiode. The device can also comprise a shutter implemented in hardware or software as a means to measure the amount of light for a certain period of time in order to measure the relative amount of light. In this way, it is possible to correct detection signals by comparing the deviations of the detection signals of devices.

When the holder drive unit 320 works, the holder 310 may be displaced forward and backward. So, when the holder 310 moves backward by a predetermined distance, the standard block 360 fixed to the holder 310 is positioned on the optical reader 410 to be described later. Therefore, the optical reader 410 can capture the fluorescent signal of the standard block 360.

In addition, when the holder 310 moves all the way to the rear, the lower rear part of the holder 310 is positioned on the optical reading module 400 to be described later. Therefore, when the holder 310 moves all the way to the rear with the cuvette 10 mounted on the mount channel 312 of the holder 310, the lower part of the detection chamber 16 disposed behind the cuvette 10 may be exposed to the optical reading module 400 through the inspection hole 314.

Since the holder 310 is guided by the holder guide unit 330, the displacement of the holder 310 can be stably made without shaking. In particular, as the pulley-belt type holder drive unit 320 is provided, the vibrations and the foreign substances due to the friction of movement can be prevented, so that more accurate inspection can be made compared to when the gear type holder is used.

Hereinafter, the optical reading module 400 will be described in detail.

The optical reading module 400 is provided to measure the signal of the reaction result in the cuvette 10. Preferably, the optical reading module 400 may include an optical reader 410, a reader drive unit 420, and a reader guide unit 430.

An optical analysis is carried out by the optical reading module 400. Such an optical analysis includes measuring a fluorescence signal, visible color and chemiluminescence of the reaction result. The definition of each signal can be referred to.

The optical reader 410 is disposed under the holder 310 when the holder 310 is moved to the rear. Therefore, when the holder 310 moves backward with the cuvette 10 accommodated in the holder 310, the detection chamber 16 of the cuvette 10 is positioned on the optical reader 410. Therefore, the fluorescence value for the reaction product in the detection chamber 16 can be measured by the optical reader 410.

The optical reader 410 reads a signal of the reaction result of the detection chamber 16 of the cuvette 10 so that a specific target analyte contained in a sample can be analyzed qualitatively and/or quantitatively.

In one embodiment of the present invention, the optical reader 410 of the optical reading module detects a fluorescent signal. It is configured to inspect the light of a specific wavelength and read the emitted light according to the type of the fluorescent material used for the detection of the analyte according to an embodiment of the present invention.

Figure 16A:
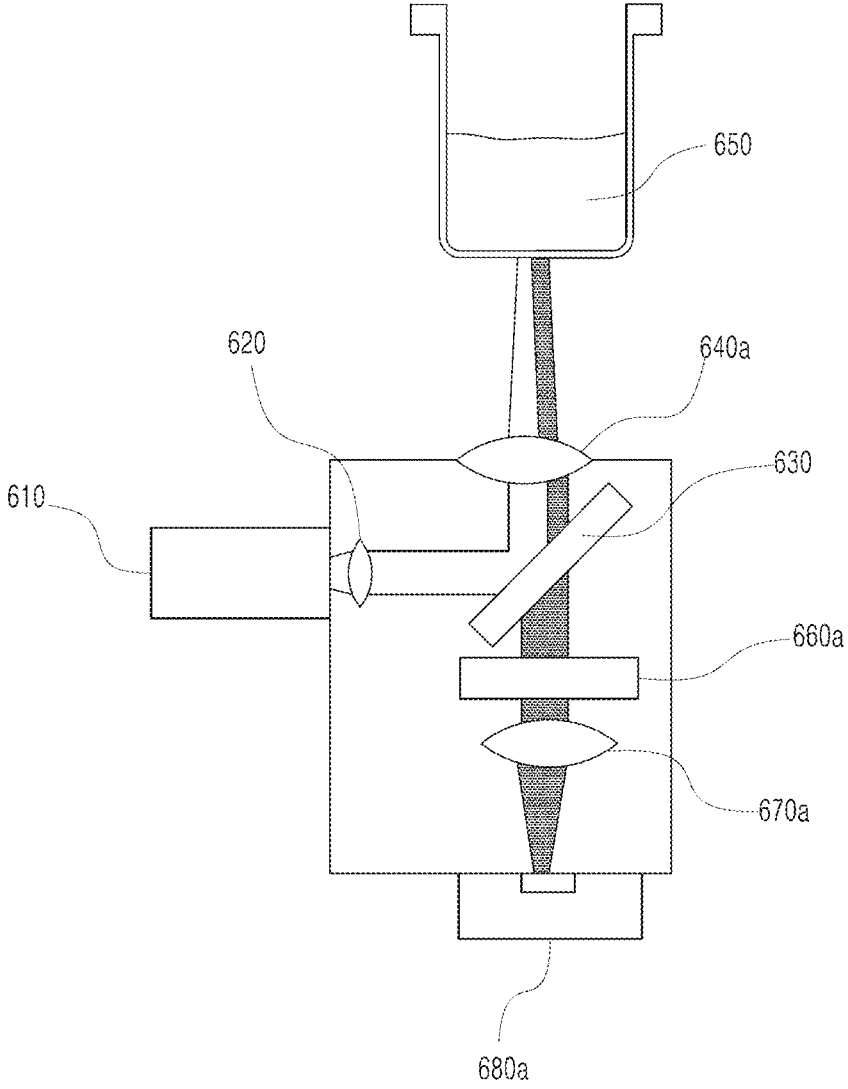
FIGS. 16a and 16b are diagrams illustrating a fluorescent optical system and a chemiluminescence optical system, respectively, which can be deployed in a device according to an embodiment of the present invention.

For example, it may include a configuration as shown in FIG. 16a. In order to analyze the reaction product 650, the optical reader 410 includes a light source 610, a collimating lens 620, a beam splitter 630, a focusing lens 640a, a filter 660a, a focusing lens 670a and a photo detector 680a.

The optical reader 410 may be provided with a light source 610 capable of sufficiently exciting a fluorescent material, that is, a predetermined light emitting element, in order to measure the fluorescent signal whose output can be controlled. As examples of such a light emitting element, there are a Xenon lamp, a UV laser and a light emitting diode (LED). In one embodiment of the present invention, an LED is used. LEDs are inexpensive and makes equipments compact compared to Xenon lamps, UV lasers, etc. In an embodiment of the present invention, when using the LED, a feedback circuit is embedded to stabilize the temperature and the power supply. it makes the diffused LED emit light in parallel using two pinholes.

In particular, as mentioned above, the light is irradiated to the standard block 360 before measuring fluorescence value, and the output of the light emitting element can be adjusted to be a certain value by adjusting the gain automatically through the amount of the captured fluorescence, so that the concentration can be calculated accurately.

On the other hand, the optical reader 410 may have two or more light sources, each of which may generate the light of different wavelength from that of the other light sources. In addition, fluorescence of different wavelengths can be measured. Therefore, the diagnostic inspection methods can be applied more broadly and sensitivity can be improved.

In addition, the optical reader 410 may have a barcode scanner function. Thus, when a predetermined barcode is provided on the cuvette 10, a predetermined signal and information can be exchanged through the barcode.

In another embodiment of the present invention, the optical reader 410 of the optical reading module can measure the absorbance of the visible color of the reaction product 650. According to an embodiment of the present invention, it is configured to measure the absorbance by irradiating light to the reaction product according to the type of the material used in detection of an analyte On the other hand, the optical reader 410 includes a light source capable of emitting a light of an absorbing wavelength region suitable for measuring the absorbance of the visible color, the output of which can be controlled. As examples of such light emitting elements, there are an LED, a laser and a lamp having an absorbing wavelength band as that of a white light source, but the present invention is not limited thereto.

In another embodiment of the present invention, the optical reader 410 measures a chemiluminescent signal of the reaction product. According to an embodiment of the present invention, It is configured to detect the light emitted according to the type of chemiluminescent material used in detection of an analyte. Since the intensity of the emitted light is measured by time, it consists of a lens for capturing light and a photodetector.

Figure 16B:
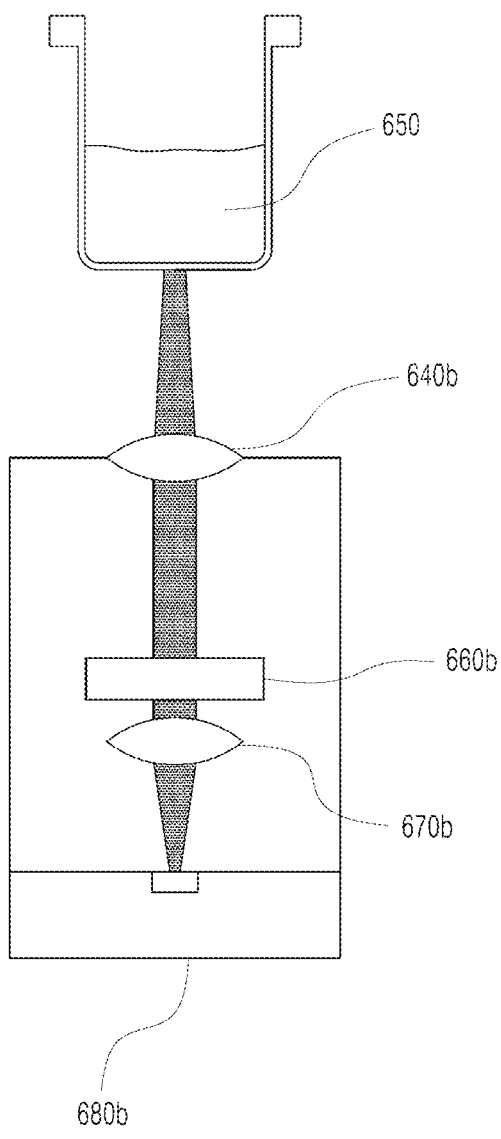

For example, it is configured as shown in FIG. 16b. To analyze the reaction result 650, the optical reader 410 includes a focusing lenses 640b and 670b and a photodetector 680b. The optical reader may further include a filter 660b for the more precise analysis. In this case, the optical reader 410 does not include a light emitting element or a light source, and instead the optical reader includes a photodetector 680b such as a photo multiplier tube (PMT) and Avalanche photodiode.

In addition, in order to measure the relative light amount, a shutter implemented in hardware or software may be provided as a means for measuring the light amount for a predetermined period of time. So, the deviations of detection signals of devices are compared to correct them.

The reader drive unit 420 is provided inside the housing 100. The reader drive unit moves the optical reader 410 to position the optical reader 410 on one of the plurality of cuvettes 10, so that the sample in the corresponding cuvette 10 may be inspected. That is, the reader drive unit 420 can move the optical reader 410 according to the position of the inspection hole 314 of the holder 310.

For example, the reader drive unit 420 comprises a predetermined driving motor 422 for moving the optical reader 410 leftward and rightward, a driven pulley 424, and a predetermined bracket for connecting the driven pulley 424 to the optical reader 410. So, the optical reader 410 may move according to the operation of the driving motor.

The reader guide unit 430 is provided to guide the optical reader 410 to be displaced leftward and rightward. The reader guide unit 430 may include a predetermined guide rail and a predetermined guide unit guided along the guide rail and fixed to the optical reader. Therefore, the optical reader can be accurately guided leftward and rightward in one direction.

As described above, in this case, when the holder 310 moves backward by a predetermined distance, the standard block 360 at the rear lower part of the holder 310 is positioned on the optical reader 410 of the optical reading module 400. Therefore, first, the optical reading module 400 detects the fluorescence signal captured in the standard block 360 as standard fluorescence.

Subsequently, when the holder 310 moves all the way to the rear with the cuvette 10 mounted on the mount channel 312 of the holder 310, the lower part of the detection chamber 16 disposed behind the cuvette 10 is exposed to the optical reader 410 through the inspection hole 314 so as to perform the optical measurement.

At this time, as described above, represented is the ratio of the fluorescent signal captured by the standard block 360 to the fluorescent signal captured by the detection chamber 16. The optical reading module 400 may have a predetermined repetitive measurement algorithm and a predetermined algorithm for comparing the above ratio with the data embedded as a master calibration graph so as to calculate the concentration of an analyte in a sample.

As described above, the fluorescence value of the standard fluorescence mounted on the standard block 360 is compared with the fluorescence value of the sample so as to perform measurement, Thus, an accurate measurement can be made. In other words, according to the general prior art, the fluorescence values vary as the devices vary. In order to reduce the variations, it is necessary to take a calibration process that reduces the variation of devices in most QC stages. Despite this process, however, it is difficult to completely eliminate these variations due to the variation of devices or of reagents. But, in the present invention, the above-described problem will be solved because the standard fluorescence mounted on the standard block 360 serves as a reference.

Figure 14A:
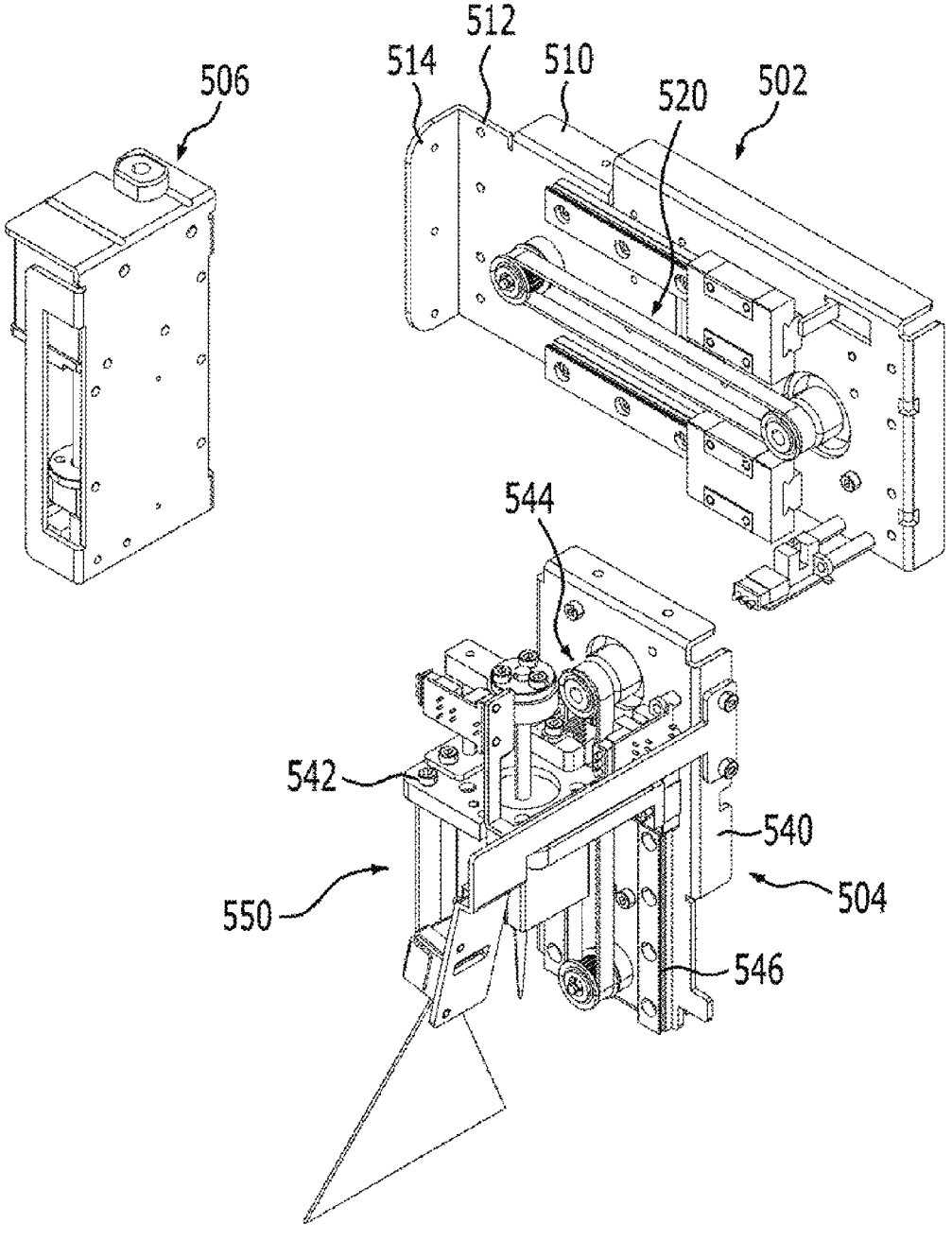
FIGS. 14a and 14b show the structure of the dispenser module in the automated liquid immunoassay device according to an embodiment of the present invention.
Figure 14B:
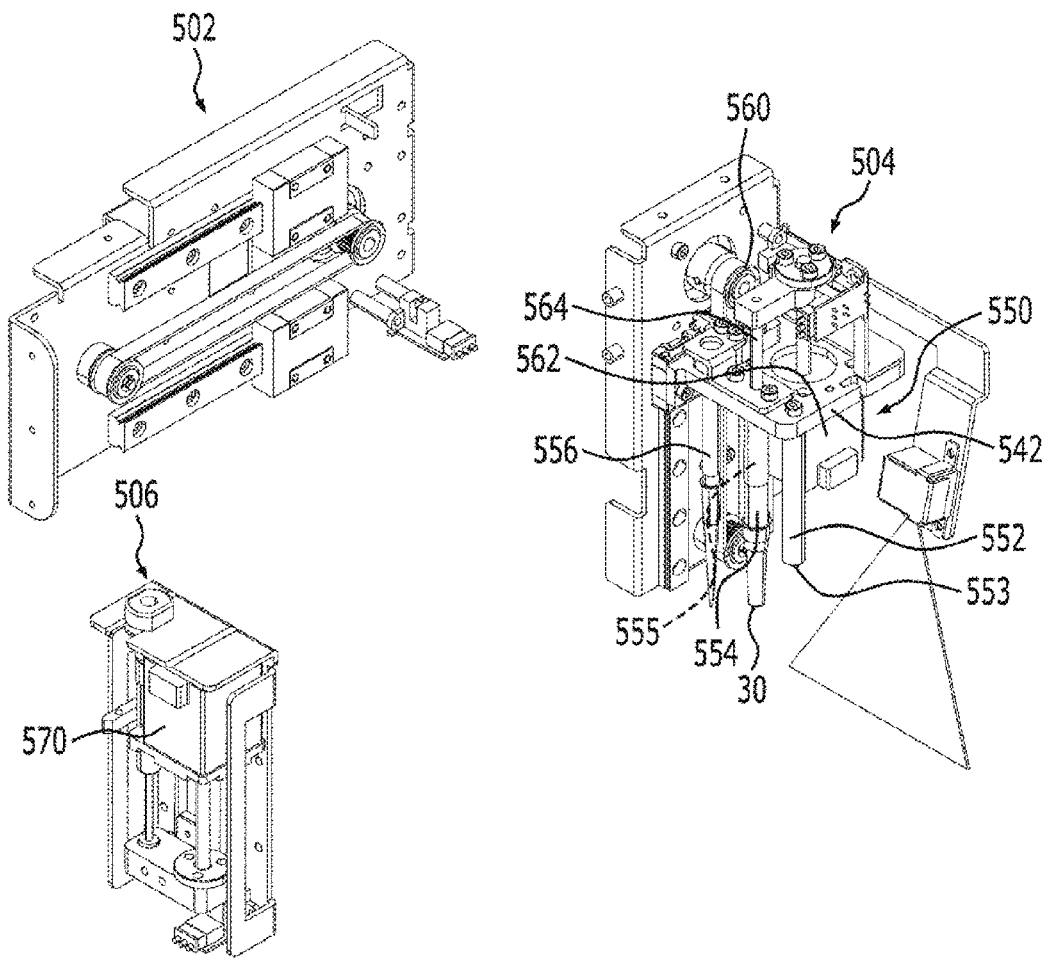

Hereinafter, the dispenser module 500 will be described. FIGS. 14a and 14b show the structure of the dispenser module 500 in the automated liquid immunoassay device 1 according to an embodiment of the present invention, which are from different angles.

The dispenser module 500 is a module for distributing, dispensing, and washing samples, reagents, and/or reactants.

The dispenser module 500 includes a drive unit 502, a dispenser unit 504 and a pump unit 506.

The drive unit 502 will be described first.

The drive unit 502 moves the dispenser unit 504 horizontally leftward and rightward. Accordingly, the dispenser unit 504 is horizontally moved by the drive unit 502, so that the dispenser unit 504 is positioned in a specific chamber on any of the plurality of cuvettes 10 disposed in parallel under the drive unit.

The drive unit 502 may include a fixed body 510 and a horizontal drive unit 520.

The fixing body 510 has a predetermined area and can extend horizontally leftward and rightward. The fixing body 510 may include a front body 512 extending horizontally leftward and rightward, and a side body 514 provided on one side of the front body 512. The pump unit 506 is fixed to a side body 514.

The horizontal drive unit 520 is disposed on the fixing body 510 and is a driving means for horizontally leftward and rightward moving the dispenser unit 504 to be described later. The horizontal drive unit 520 may include a predetermined driving motor that generates power, and a predetermined movable bracket can that be displaced horizontally leftward and rightward by the driving motor. In addition, a predetermined guide means 530 may be provided to guide the displacement of the movable bracket. In addition, it may include a predetermined driven pulley member for transmitting power.

Next, the dispenser unit 504 will be described. The dispenser unit 504 includes a horizontal movable body 540, a vertical movable body 542, a vertical drive unit 544 and an arm unit 550.

The horizontal movable body 540 is connected to the horizontal drive unit 520. As described above, the horizontal drive unit 520 includes a predetermined movable bracket. And, the horizontal movable body 540 is connected to the movable bracket to be displaced horizontally leftward and rightward.

The vertical movable body 542 is disposed in front of the horizontal movable body 540. The vertical movable body may be displaced vertically upward and downward by the vertical drive unit 544.

The vertical drive unit 544 is disposed on the horizontal movable body 540 and is a driving means for moving the vertical movable body 542 vertically upward and downward. The vertical drive unit 544 may also include a predetermined driving motor that generates power and a predetermined movable bracket that can be displaced horizontally leftward and rightward by the driving motor. In addition, it may further include a predetermined guide means 546 for guiding the vertical displacement of the movable bracket. In addition, it may further include a predetermined driven pulley member that transmits power.

The arm unit 550 is a member that can be moved vertically upward and downward by the vertical drive unit 544 and be moved horizontally leftward and rightward by the drive unit 502 at the same time. The arm unit 550 includes a punch arm 552, a collection arm 556 and a straw arm 554, which are connected to the vertical movable body 542 and extended downward at positions horizontally spaced from each other. Accordingly, the arm unit 550 may constitute an all-in-one module into which the punching arm 552, the collection arm 556, and the straw arm 554 are integrated.

The punch arm 552 includes a punch tip 553 at bottom, and is a member for punching the sealing cover of the cuvette 10 so as to open the cuvette. The punch arm punches the sealing part that covers the corresponding chamber of the cuvette 10.

The vertically penetrated straw arm 554 has a hollow 555. The outer diameter of the straw arm 554 is so large that the straw arm can be inserted into the insertion hole of the washing tip 30.

The collection arm 556 is provided to fix the dispensing tip 20 to the bottom of the collection arm. The outer diameter of the collection arm 556 is so large that the collection arm can be inserted into the dispensing tip 20.

Preferably, the punch arm 552, the straw arm 554 and the collection arm 556 may be arranged in parallel forward and backward.

The washing unit 560 includes a driving motor 562 and a magnetic beam 564.

The driving motor 562 is fixed to the vertical movable body 542 and connected to the magnetic beam 564 so as to displace the magnetic beam 564 vertically upward and downward. On the other hand, it is not necessarily limited to the driving motor 562, it does not matter if provided is a predetermined driving device capable of displacing the magnetic beam 564 vertically upward and downward.

The magnetic beam 564 has a bar shape extending vertically upward and downward and is disposed in the vertical hollow 555 of the straw arm 554. The magnetic beam 564 is magnetic and can be displaced by the driving motor 562 vertically upward and downward, so that possible is a mag-extraction that separates unreacted materials by magnetism.

The pump unit 506 is fixed to the side body 514 of the drive unit 502. The pump unit 506 is connected to the collection arm 556 of the dispenser unit 504 through predetermined pipe (not shown). So, when the dispensing tip 20 connected to the collection arm 556 is inserted into the chamber of the cuvette 10, the pump unit provides suction power or discharge power. Specifically, when the cuvette 10 is positioned at a specific point by the cuvette module 300 and the dispensing tip 20 positioned on the chamber of the cuvette 10 is introduced into the chamber by the drive unit 502, the dispensing tip 20 can be provided with suction power or discharge power. Preferably, the pump unit 506 includes a motor 570 capable of rotary microstep control, and can control the amount of the sample accurately when sample, reagent or reaction product is inhaled from or discharged to the dispensing tip 20.

Figure 15A:
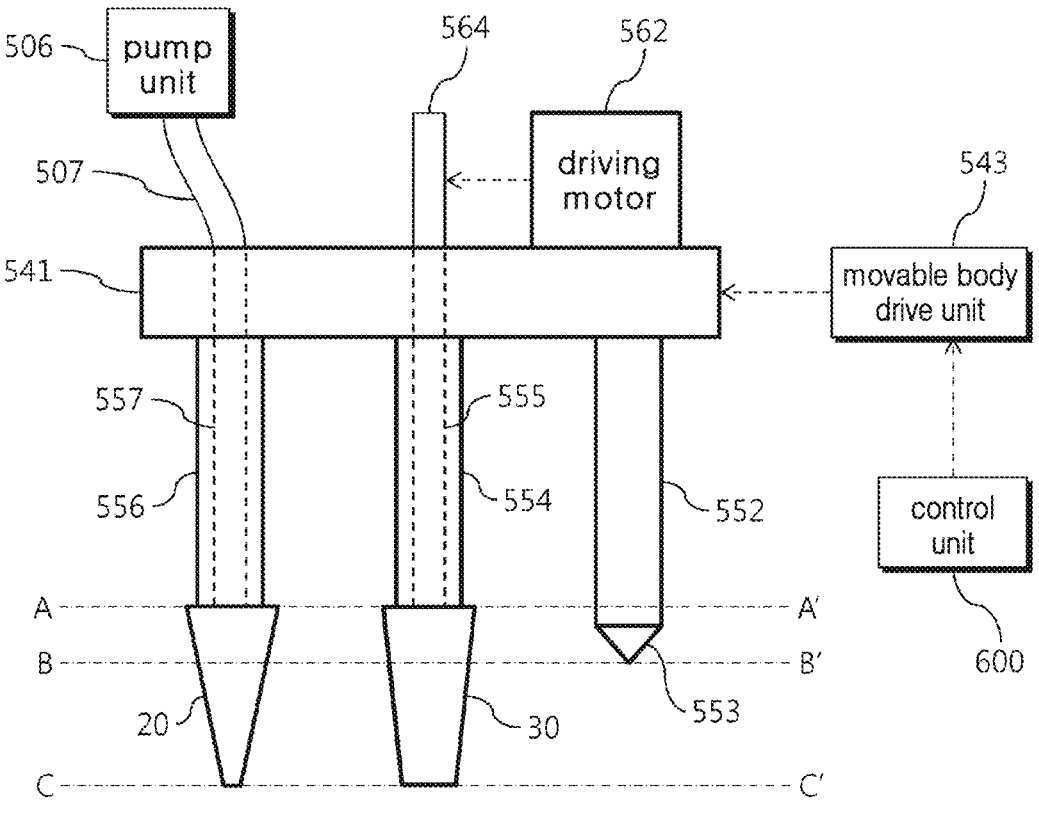
FIG. 15a is a block diagram illustrating the schematic structure of a dispenser module in the automated liquid immunoassay device according to another embodiment of the present invention.

FIG. 15*a* is a block diagram illustrating the schematic structure of a dispenser module in the automated liquid immunoassay device according to another embodiment of the present invention.

The dispenser module includes a movable body 541, a movable body drive unit 543, and a control unit 600. The control unit 600 controls the movable body drive unit 543 to move the movable body 541 to a desired position.

A punch arm 552, a straw arm 554 and a collection arm 556 are fixed to the movable body 541. Therefore, as the movable body moves, the punch arm, the straw arm and the collection arm are all moved.

A punch tip 553 is provided at the lower part of the punch arm 552. When the punch arm punches the sealing potion of the lower cuvette, the straw arm and the collection arm that are fixed to the punch arm and the movable body 541 and move together should not interfere with the lower cuvette. That is, the length B from the lower part of the movable body to the lower part of the punch arm 552 should be longer than the length A of the straw arm and the collection arm. The proper length can be set so that the straw arm and the collection arm do not touch the cuvette even if the punch arm is lowered to the end to punch the sealing part of the cuvette.

In case that the straw arm 554 with the washing tip 30 or the collection arm 556 with the dispensing tip 20 works with the cuvette, the punch arm 552 should not interfere with the lower cuvette. Therefore, the length B from the lower part of the movable body to the lower part of the punch arm 552 should be shorter than the length C from the lower part of the movable body to the end part of the washing tip mounted on the straw arm or to the end part of the dispensing tip mounted on the collection arm. That is, the height of the washing tip and the dispensing tip should be greater than the sum of the length of the punch arm and the depth of each chamber in the cuvette. The length of each tip can be set to an appropriate length in consideration of the mounting position of each arm and the distance of smooth operation of it in each chamber.

The collection arm 556 can mount the dispensing tip 20 at its bottom by fixing it. A collection hollow 557 that penetrates vertically upward and downward is provided inside the collection arm. The hollow of the collection arm is connected to the pump unit 506 through a pipe 507. The pump unit 506 may provide the dispensing tip with suction power and discharge power through the pipe and the hollow of the collection arm.

The straw arm 554 can mount the washing tip 30 at its bottom by fixing it. A vertical hollow 555 that penetrates vertically upward and downward is provided inside the straw arm. A magnetic beam 564 that can move vertically upward and downward is positioned in the hollow of the straw arm. A driving motor 562 is provided to displace the magnetic beam vertically upward and downward. It is preferable to fix the driving motor 562 to the movable body so that the magnetic beam can move relative to the straw arm fixed to the movable body.

The driving motor and the magnetic beam can be connected with each other by means of a rack, a pinion, a linear actuator using a ball screw and a speed reducer using gear coupling.

Figure 15B:
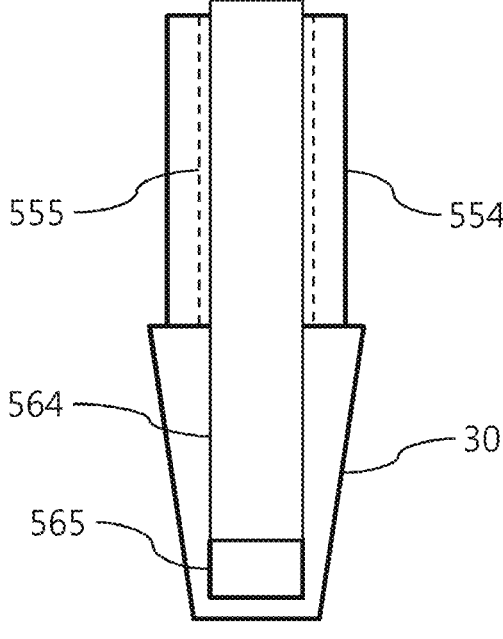
FIG. 15b is an enlarged view showing in detail the washing tip part of the dispenser module in an automated liquid immunoassay device according to another embodiment of the present invention.

FIG. 15*b* is an enlarged view showing in detail the washing tip part of the dispenser module in an automated liquid immunoassay device according to another embodiment of the present invention.

A magnetic beam 564 is disposed in the vertical hollow 555 of the straw arm 554. The magnetic beam 564 may include a permanent magnet 565 at the lower part which is the opposite end of the part connected to the driving motor 562. The permanent magnet 565 preferably has the same cross-sectional shape as the magnetic beam to which the permanent magnet is attached. If the magnetic beam is cylindrical, a cylindrical permanent magnet with the same diameter can be used. When the magnetic beam 564 is lowered by the driving motor 562, a permanent magnet may be disposed inside the washing tip 30 fitted to the straw arm 554.

When considering the size of the chamber of the cuvette, the permanent magnet 565 preferably has a diameter between 2 mm and 8 mm. If the length of the permanent magnet is 5 mm or more, the magnetic beads can be collected, but it is preferable to be 10 mm or more in order to collect the magnetic beads required for measurement within 1 minute. More preferably, in case that it is 30 mm or more, the sufficient amount of magnetic beads can be collected within 40 seconds. The various shapes such as round, square and oval can be selected as the shape of the permanent magnet to use according to the purpose.

Hereinafter, the operation of the automated liquid immunoassay device 1 according to an embodiment of the present invention will be described with reference to FIGS. 17 through 20.

Figure 17:
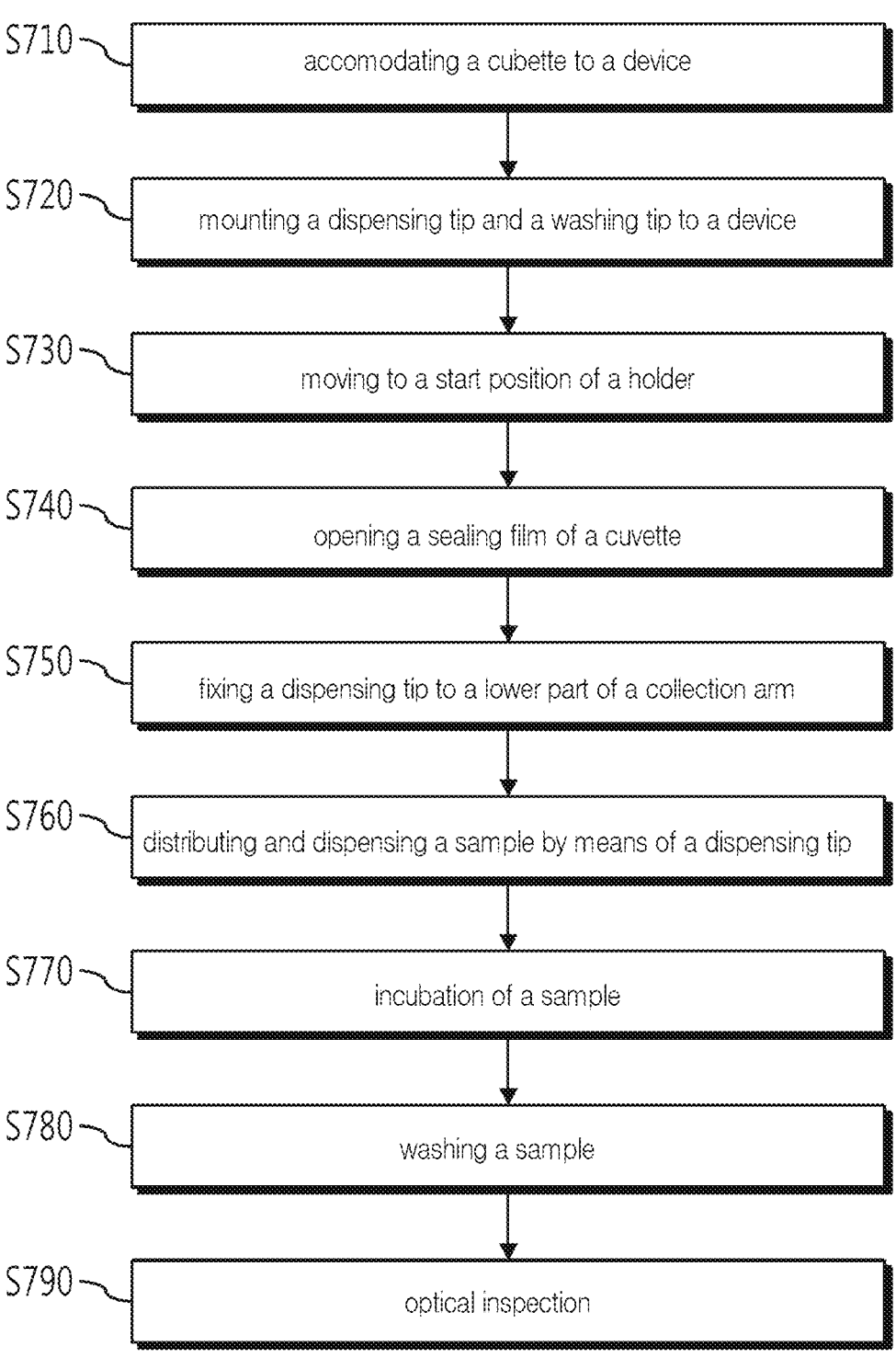
FIG. 17 is a flowchart showing the overall process of the automated liquid immunoassay method according to an embodiment of the present invention.

FIG. 17 is a flowchart showing the overall process of the automated liquid immunoassay method according to an embodiment of the present invention.

First, the cuvette 10 is accommodated in the mounting channel 312 of the holder 310 of the device 1 (S710). Then, the dispensing tip 20 and the washing tip 30 are mounted to the dispensing tip fitting hole 21 and the washing tip fitting hole 31 formed in the cuvette, respectively (S720). Actually, the dispensing tip 20 and the washing tip 30 may be mounted either before or after the cuvette 10 is accommodated in the mounting channel 312. Subsequently, the holder 310 is moved backward by the start command of the device (S730).

Subsequently, the dispenser module 500 operates to punch and open the sealing film (not shown) of the cuvette 10 (S740). In the punching process, a punch arm 552 is used. This punching process will be described. First, the punch arm 552 is positioned on the cuvette 10 by the drive unit, and then, the punch arm 552 is moved upward and downward by the vertical drive unit 544 to move the cuvette 10. To punch the sealing film. In this process, the cuvette module 300 is operated so that the cuvette 10 moves forward or backward, so that a plurality of chambers provided in the cuvette 10 can be punched. This punching step will be described. First, the punch arm 552 is positioned on the cuvette 10 by the drive unit. And then, the punch arm 552 is moved vertically upward and downward by the vertical drive unit 544 to punch the sealing film of the cuvette 10. In this process, the cuvette module 300 moves the cuvette 10 horizontally forward or backward so as to punch a plurality of chambers provided in the cuvette 10.

Subsequently, after the punching operation is completed, the cuvette module 300 and dispenser module 500 make the collection arm 556 positioned on the dispensing tip 20 fixed to the cuvette 10. And then, the collection arm 556 moves downward to fit and fix the dispensing tip 20 to the lower part of the collection arm 556 (S750). Thereafter, the sample and/or reagent is distributed and dispensed by means of the dispensing tip 20 (S760).

The dispensing process will be described. First, the movable body 541 to which a collection arm is fixed is moved to introduce the dispensing tip into the sample solution. Then, the pump unit 506 connected to the hollow of the collection arm applies suction power to the dispensing tip 20 so as to collect a sample from the sample chamber. Next, the movable body drive unit 543 moves the collection arm fixed to the movable body to the reaction chamber. At this time, the sample in the dispensing tip attached to the collection arm is also transferred to the reaction chamber. That is, the collected sample can be transferred to the reaction chamber. And then, the pump unit 506 applies discharge power to the dispensing tip 20 so that the sample is discharged into the reaction chamber. So, dispensing is completed.

In this process, as in the previous punching process, the cuvette module 300 may move the cuvette 10 horizontally forward or backward and the vertical drive unit 544 may move the dispensing tip 20 vertically upward and downward. At the same time, the pump unit 506 distributes and dispense to the dispensing tip 20. In addition, in the distributing and dispensing process, the sample and/or reagents are mixed owing to the pump unit 506, and the desired reaction can occur in the reaction chamber 14 of the cuvette.

The reaction process occurring in the cuvette 10 as described above includes a plurality of steps, and requires at least two incubation times per cuvette (S770). Incubation may applies power to the heat plate 316 of the holder 310 in which the sample is mounted, so that the sample dispensed to the reaction chamber may be maintained to be at a constant temperature.

Therefore, during the first incubation time, the dispensing tip 20 used in the first cuvette is removed by the remover plate 350 and positioned in the dispensing tip fitting hole 21 of the first cuvette in order to start the reaction of the second cuvette. After completion of the first incubation, it is used again for the reaction of the next step of the first cuvette.

The incubated sample is subjected to a washing process (S780). After washing, the sample containing the magnetic beads from which impurities have been removed is moved to the detection chamber for an optical inspection process and then is used for analysis through (S790).

FIG. 18 is a flowchart showing the washing process in the automated liquid immunoassay method according to an embodiment of the present invention.

The washing process includes the steps of: collecting magnetic beads, moving the collected magnetic beads to the washing solution, and removing impurities.

That is, first, a washing tip into which a magnetic beam is inserted is introduced into a sample solution containing magnetic beads so as to collect magnetic beads in the sample solution onto the surface of the washing tip (S820 to S845). Next, the washing tip which the magnetic beads are collected onto the surface of and the magnetic beam is inserted into is moved to the washing solution and introduced into the washing solution (S850). Then, the driving motor connected to the magnetic beam moves the magnetic beam upward, and moves the washing tip upward and downward several times so as to scatter the magnetic beads collected onto the washing tip in the washing solution (S860). After that, the magnetic beams are inserted into the washing tip so that collected are the magnetic beads in the washing solution again (S870). If it is less than the predetermined number of times of washings, the washing tip with the collected magnetic beads is moved to a new washing chamber and then the above-mentioned process can be repeated until it reaches the predetermined number of times of washings (S880). When the washing process is completed, an optical measurement can be performed in the detection chamber (S890).

The washing process can be performed in various ways. The driving motor connected to the magnetic beam moves the magnetic beam horizontally upward and downward several times without moving the washing tip so as to repeat distributed collection of the magnetic beads collected in the washing tip in the washing solution. So, removed are impurities that are not bond with the magnetic beads.

Meanwhile, the step of collecting the magnetic beads in the sample solution can be divided as follows. First, the washing tip 30 is fixed to the lower part of the straw arm 554 which a hollow penetrates vertically upward and downward inside (S820). Then, the movable body 541 with a fixed straw arm is moved downward to introduce the washing tip into a sample solution containing magnetic beads (S830). Next, a driving motor 562 fixed to the movable body move to insert a magnetic beam 564 positioned in the hollow of the straw arm into the washing tip at the lower part of the straw arm (S840). Thereafter, the movable body drive unit 543 moves the movable body fixed with the straw arm and the magnetic beam together so as to move the washing tip which the magnetic beam is inserted into in the sample solution containing the magnetic beads (S845).

The above-described step is as follows. When it is completed to distribute, dispense and react the sample and reagent, the dispensing tip 20 is removed from the collection arm 556 by the remover plate 350 (S810). Subsequently, the washing tip 30 is inserted into the straw arm 554 (S820). The washing tip 30 is introduced into the reaction chamber 14 (S830). And then, a magnetic beam 564 is introduced into the washing tip 30 so that the magnetic beads in the reaction chamber 14 are collected onto the surface of the washing tip 30 (S840). At this time, the reactants bonded with the magnetic beads are captured together. In order to collect the magnetic beads more efficiently, the washing tip and the magnetic beam can be moved together in the sample solution (S845). The washing tip 30 is moved to the washing chamber 15 (S850), when the magnetic beam 564 is moved upward by the driving motor 562 so that the magnetic beam 564 is spaced apart from the washing tip 30, the magnetic beads collected onto the washing tip 30 are scattered in the washing chamber 15 (S860). At this time, the washing tip can be moved vertically upward and downward several times to scatter the magnetic beads collected onto the washing tip in the washing solution well. When the magnetic beam 564 is moved downward to the washing tip 30 again, the magnetic beads are collected again onto the washing tip 30 (S870). The vertical moving of the magnetic beam is made as many as a predetermined number of washing (S880). As the magnetic beam moves vertically, impurities without magnetism may be removed by the reciprocating move of the magnetic beads in the washing chamber. When the sample is washed, the reaction product is transferred to the detection chamber 16 (S890).

Figure 22:
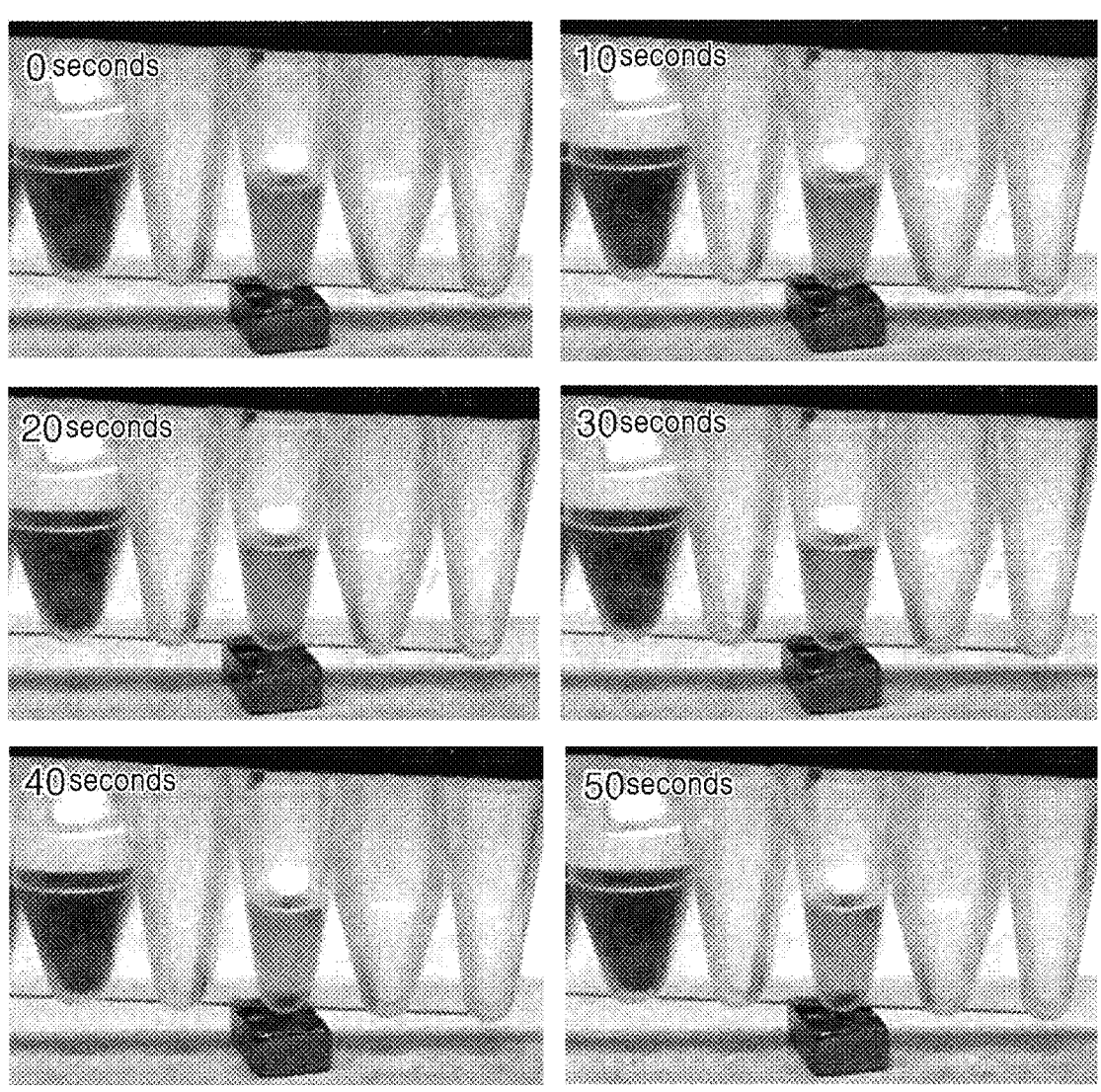
FIG. 22 is photographs showing the influence from permanent magnets on the sample having the magnetic beads used in the automated liquid immunoassay method according to an embodiment of the present invention.

FIG. 22 is photographs showing the influence from permanent magnets on the sample having the magnetic beads used in the automated liquid immunoassay method according to an embodiment of the present invention. A permanent magnet was placed under a solution containing a sample having magnetic beads at a high concentration so as to observe the effect over time. In the photo showing the state at 0 second, the magnetic beads are scattered, so that it looks like yellow solution overall. Over time, the magnetic beads are pulled toward the permanent magnet at the bottom, so that the solution gets transparent more and more and it looks dark yellow at the bottom. About 50 seconds later, the magnetic beads are pulled sufficiently to the permanent magnet at the bottom.

Figure 23:
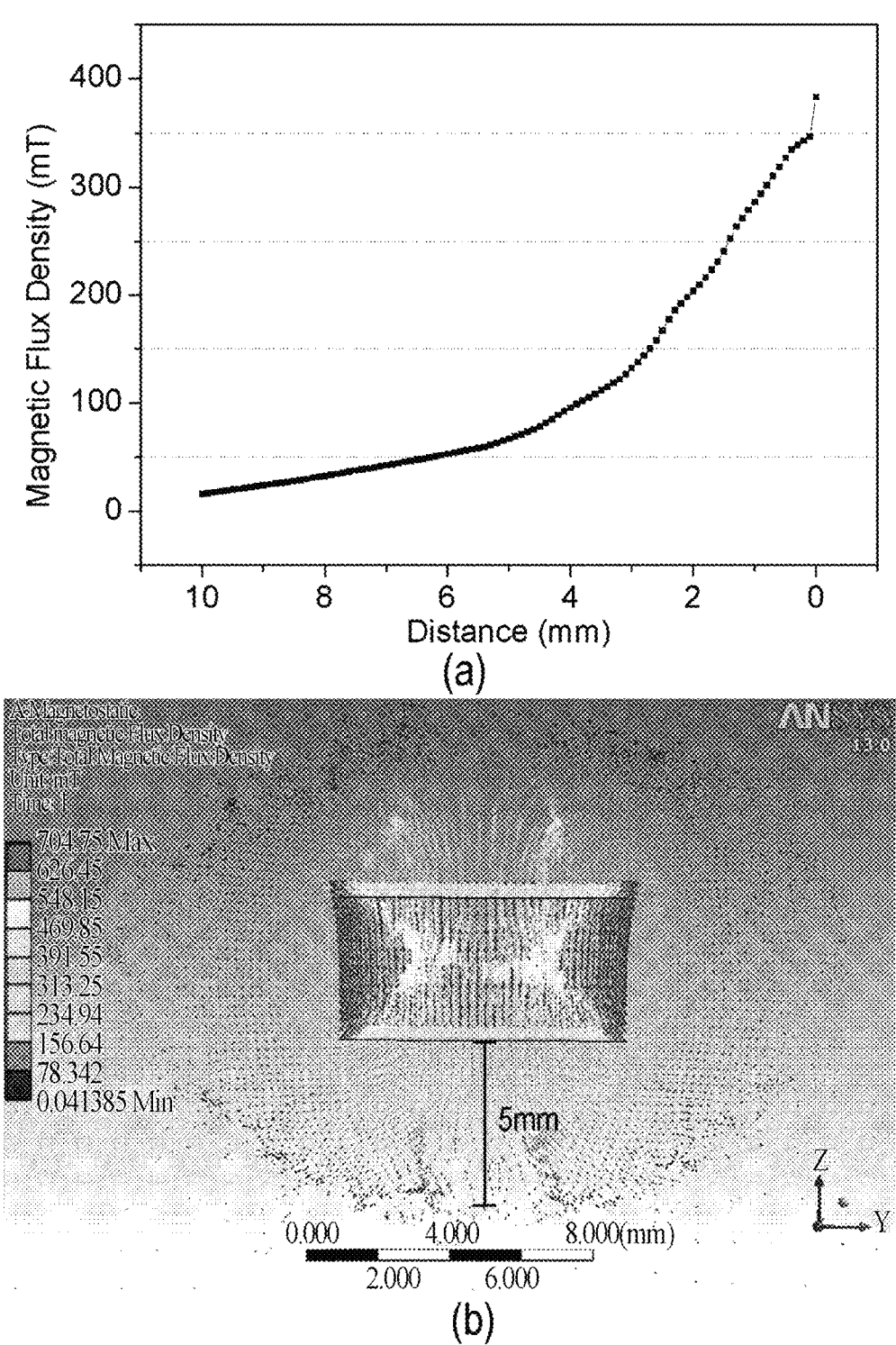
FIG. 23 is a graph showing the magnetic field strength of the permanent magnet used in the automated liquid immunoassay method according to an embodiment of the present invention.

FIG. 23 is a graph showing the magnetic field strength of the permanent magnet used in the automated liquid immunoassay method according to an embodiment of the present invention. The permanent magnet used in the simulation is a cylindrical magnet with a diameter of 8 mm and a thickness of 4 mm. FIG. 23 shows a simulation result for a magnetic field of 3700 Gauss and a coercive force of 846 KA/m.

Referring to FIG. 23, (a) shows the strength of the magnetic field according to the distance from the magnet. It shows that the magnetic field intensity decreases as the distance from the magnet increases. That is, it shows the strength of the magnetic field of 200 mT at the position 2 mm away from the magnet. If it exceeds 2 mm, the strength of the magnetic field gets weaker and the force to pull the magnetic beads gets reduced too. The maximum height of the solution is about 10 mm, but the magnetic force is negligible at a position 10 mm away from the magnet.

Referring to FIG. 23, (b) shows the magnetic field strength according to the position around the magnet. It shows that the stronger magnetic field widely ranges in vertical direction of the magnet rather than in the circumferential direction of the magnet outside the magnet except for the inside of the magnet, when the range of the green and light blue parts outside the magnet are considered. As a result, in case that a cylindrical permanent magnet is used, if used is the magnetic fields from the lower and upper parts of the magnet rather than that of the cylindrical side of the magnet, it has a greater influence on the magnetic beads and the magnetic beads can be collected or washed more quickly.

Figure 24:
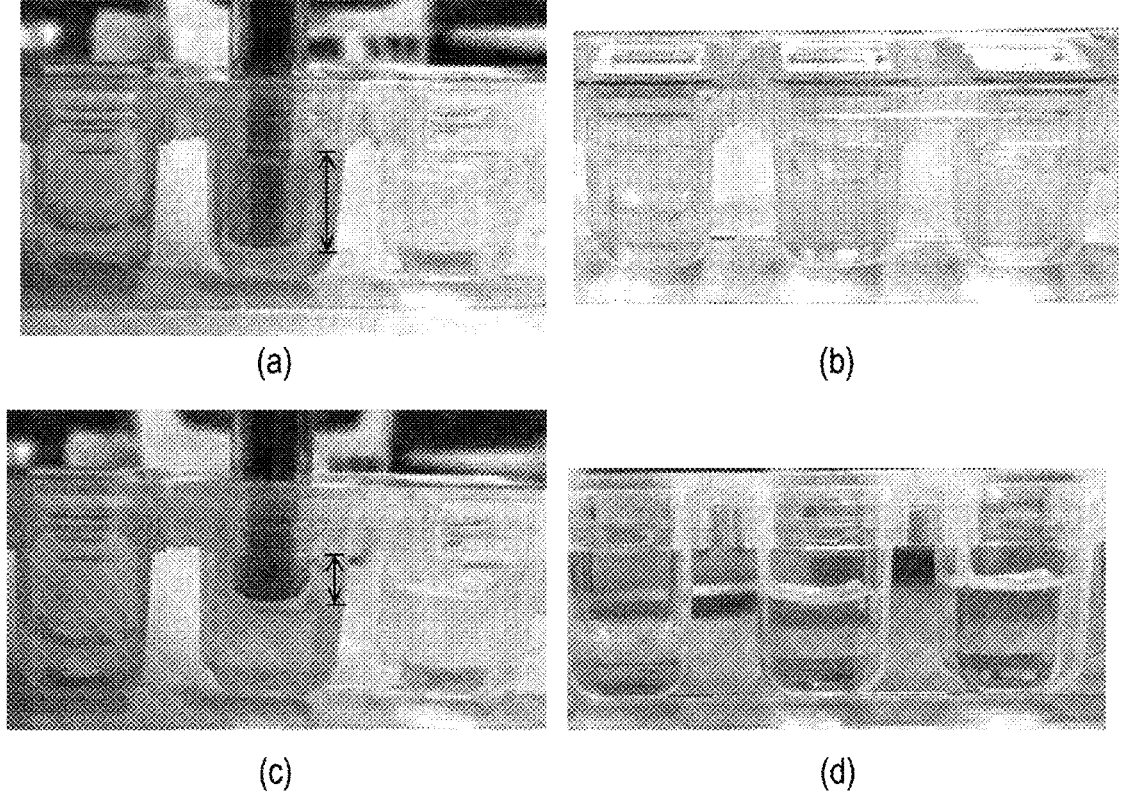
FIG. 24 is photographs showing the position of the washing tip used in the automated liquid immunoassay method according to an embodiment of the present invention.

FIG. 24 is photographs showing the position of the washing tip used in the automated liquid immunoassay method according to an embodiment of the present invention. In these photos, magnetic beads were added at high concentration for visualization.

In the automated immunoassay method according to an embodiment of the present invention, the washing tip can be taken out after keeping it contacting the bottom of the washing chamber for a certain period of time as shown in FIG. 24 (a). In this case, 45 seconds later, most of magnetic beads can be collected as shown in FIG. 24 (b).

In the automated immunoassay method according to another embodiment of the present invention, the washing tip can be taken out after keeping it in the middle of the solution contained in the washing chamber for a certain period of time as shown in FIG. 24 (c). In this case, 45 seconds later, almost all the magnetic beads can be completely collected as shown in FIG. 24 (d). Thus, if the used magnet is thin, the stronger magnetic field more widely ranges in vertical direction of the magnet so that the more magnetic beads can be pulled more quickly.

In the automated immunoassay method according to another embodiment of the present invention, the position of the washing tip is changed when the magnetic beads are collected and washed. That is, since the magnetic force of the permanent magnet varies depending on the distance, the magnetic beads can be collected more efficiently when the washing tip containing the permanent magnet is moved vertically upward and downward from the middle of the solution containing the magnetic beads while the magnetic beads are collected. The advantageous position for the vertical moving for collecting the magnetic beads can be selected from a range between the side and the bottom of the solution.

Also, considering the time during which the magnetic beads are pulled to the permanent magnet to be collected, the washing tip is stopped for a certain period of time until the magnetic beads are collected at a certain position in the solution containing the magnetic beads. And then, after a certain period of time, the washing tip advances a little bit and stops in solution again for a certain period of time. It is called a stepped elevation movement. By means of such a stepped elevation movement, that is, the divided operations, the magnetic beads can be more completely collected in a short time. In the divided operations, the moving distance and the stopping time may be determined in consideration of the washing time.

For example, in the case that the washing time is set to be less than or equal to 40 seconds and the moving distance of the washing tip is set to be 4 mm, the washing tip equipped with the magnetic beam is stopped for 5 seconds after the washing tip is introduced in the initial solution. And then, the washing tip is moved downward by 1 mm and stopped for 5 seconds. And then, the washing tip is moved downward by 1 mm and stopped for 5 seconds again. This process can be repeated so as to move the washing tip by 4 mm in the solution. After the washing tip moves to the bottom of the solution, the washing tip equipped with the magnetic beam is moved upward by 1 mm and stopped for 5 seconds. And then, the washing tip is moved upward by 1 mm and stopped for 5 seconds again. This process can be repeated. In this way, the magnetic beads can be completely collected in a shorter time, so that the washing process can be performed more quickly and completely.

According to an embodiment of the present invention, the washing tip into which the magnetic beam with a permanent magnet is inserted is stopped at the middle of the sample solution containing the magnetic beads so as to collect the magnetic beads. Preferably, the magnetic beads can be collected while the magnetic beam and the washing tip into which the magnetic beam is inserted are moved together upward and downward in the sample solution containing the magnetic beads. More preferably, the magnetic beads are collected more quickly and completely by means of the stepped elevation movement in which the washing tip and the magnetic beam are moved by a predetermined distance and stopped for a certain period of time, while the washing tip and the magnetic beam are moved together upward and downward in the sample solution containing the magnetic beads.

Such the method of collecting the magnetic beads onto the washing tip can be applied to the step of collecting the magnetic beads in the sample solution (S845) and also to the step of collecting the magnetic beads in the washing solution (S870) in the same manner.

Meanwhile, in the above-mentioned process, the dispensing tip 20 can be separated from the washing tip 30 by the remover module 340. That is, the dispensing tip 20 or the washing tip 30 is placed in the remover hole 354 of the remover plate 350. And then, the remover plate 350 is moved so as to place the dispensing tip and the washing tip in the depression 356. And then, if the collection arm or the straw arm is moved upward, the part of the upper end of the tip attached to the collection arm and the straw arm is blocked by the depression 356, so that the dispensing tip 20 or the washing tip 30 can be separated from the collection arm 556 or the straw arm 554.

The dispensing tip 20 can be separated from the washing tip 30 in the same way. Describing the separation of the washing tip 30 in detail, the separation can be made in the following order. The remover plate 350 is positioned between the holder 310 and the dispenser module 500. First, the remover hole 354 of the remover plate 350 is positioned over the washing tip fitting hole 21. That is, the remover plate 350 having the remover hole 355 in which the depression 356 is formed is disposed under the straw arm 554 equipped with the washing tip 30. Subsequently, the straw arm equipped with the washing tip passes through a remover hole 355 that is wider than the area of the upper end of the washing tip, so that the washing tip 30 is positioned in the washing tip fitting hole 21. Thereafter, the remover plate 350 is made to contact with the washing tip 30. That is, the depression 356 of the remover plate is positioned above the upper end of the washing tip. And then, the straw arm is moved to the upper part of the remover plate so that the upper part of the washing tip 30 is blocked by the depress of the remover plate and the washing tip can be separated from the straw arm. That is, the dispenser module 500 is move upward and the washing tip 30 is blocked by the remover plate 350, so that the washing tip 30 is separated from the straw arm 554 to be placed in the washing tip fitting hole 21.

Therefore, the dispensing tip 20 and the washing tip 30 which are separated from each other remain in the washing tip fitting hole 21 and in the dispensing tip fitting hole 31, respectively. So, after the dispensing tip 20 and the washing tip 30 are separated from each other, the sample is not mixed with other samples, so that no tips are needed to wash and the tips can be reused for the reaction of the next step in the same cuvette.

Subsequently, when the reaction product is moved into the detection chamber 16, the optical reading module 400 performs optical inspection. At this time, the optical reader 410 is positioned under the detection chamber 16. In addition, as described above, the detection chamber 16 has light transmittance, so that the optical reader 410 can perform an optical inspection on the reactants therein.

Figure 19:
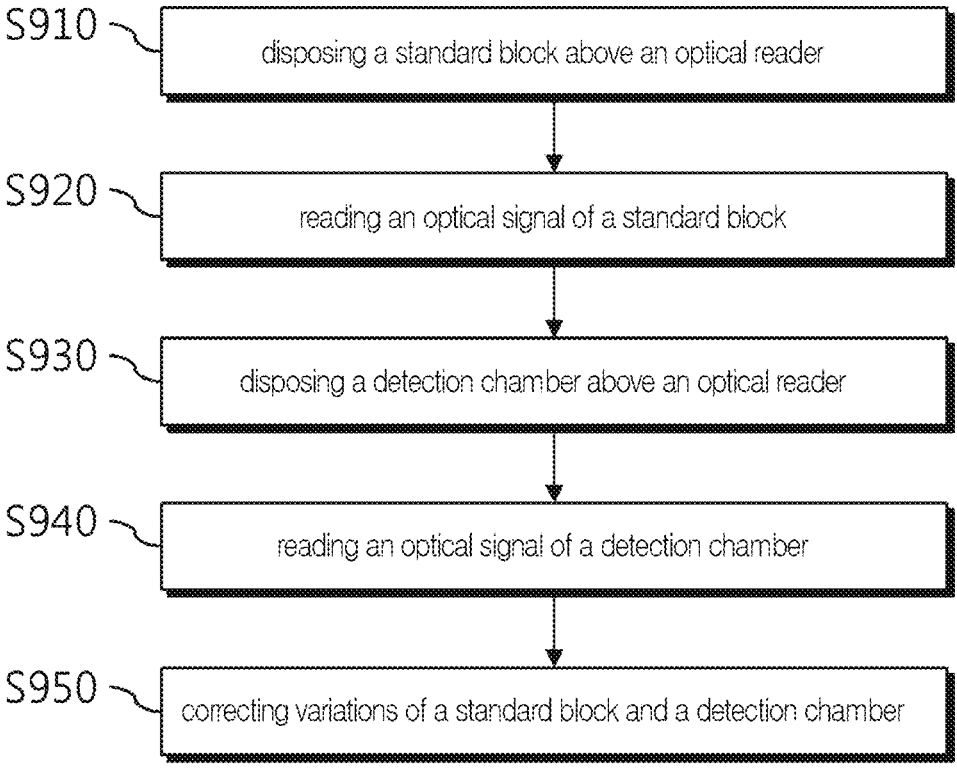
FIG. 19 is a flowchart showing the optical inspection process using a standard block in the automated liquid immunoassay method according to an embodiment of the present invention.

FIG. 19 is a flowchart showing the optical inspection process using a standard block in the automated liquid immunoassay method according to an embodiment of the present invention.

First, the standard block 360 at the rear lower part of the holder 310 is disposed above the optical reader (S910). For this, the holder 310 or the optical reader 410 can be moved so that the standard block 360 can be positioned on the optical reader 410. The optical reader 410 may perform an optical inspection on the fluorescence measurement standard material in the standard block 360 positioned at the rear part of the holder 310 so as to read the fluorescence signal of the standard material first (S920). Subsequently, an optical reader 410 is disposed under the detection chamber (S930). That is, the holder or the optical reader is moved so that the detection chamber 16 is positioned above the optical reader 410. The optical reader 410 performs an optical inspection on the sample in the detection chamber 16 through the inspection hole 314 penetrating in the vertical direction under the holder 310 equipped with the detection chamber, and reads the optical signal emitted from the sample (S940). As described above, the signal detected by the standard block 360 is used as a standard fluorescence value to correct the variation of devices (S950). That is, the signal obtained as a result by the optical inspection on the sample in the detection chamber is compared with the signal obtained as a result by the optical inspection on the standard material in the standard block. And then, the difference is analyzed to correct the result of the optical inspection on the sample in the detection chamber, so that the more accurate results can be obtained.

In addition, the device according to an embodiment of the present invention is provided in the housing and may further include a chip insertion unit (not shown) into which a chip containing analysis information is inserted. The chip inserted into the chip insertion unit works with the barcode of the cuvette. The barcode of the cuvette includes the information of the substance (item) to be analyzed and the lot information of the cuvette, and is used by the chip. The chip contains the master calibration curve necessary for calculating the concentration of the analyte and the information for driving the device according to the type of analyte in the sample, so that the optimal inspection can be performed with the barcode according to the various types of analytes. Thus, various analytes can be easily inspected with a single device, and the reproducibility and the reliability of the inspection can also be improved. The information is retrieved from the barcode through a barcode scanner that scans the barcode.

The inspection process according to an embodiment of the present invention is described in order as follows.

Here, the case that the cuvette 10 having the structure as shown in FIG. 6 is used will be described as an example. The cuvette 10 used in the inspection according to the present invention may have a structure as shown in FIG. 6. Specifically, the cuvette 10 may include a sample filling chamber 12, a buffer and dilution chamber 13 having an MB buffer chamber 13a, a chamber 13b filled with a detection buffer such as an Alkaline phosphatase (ALP), a dilution buffer chamber 13c and a dilution chamber 13d, a reaction chamber 14, and a washing chamber 15 having a first washing chamber 15a and a second washing chamber 15b.

Figure 20:
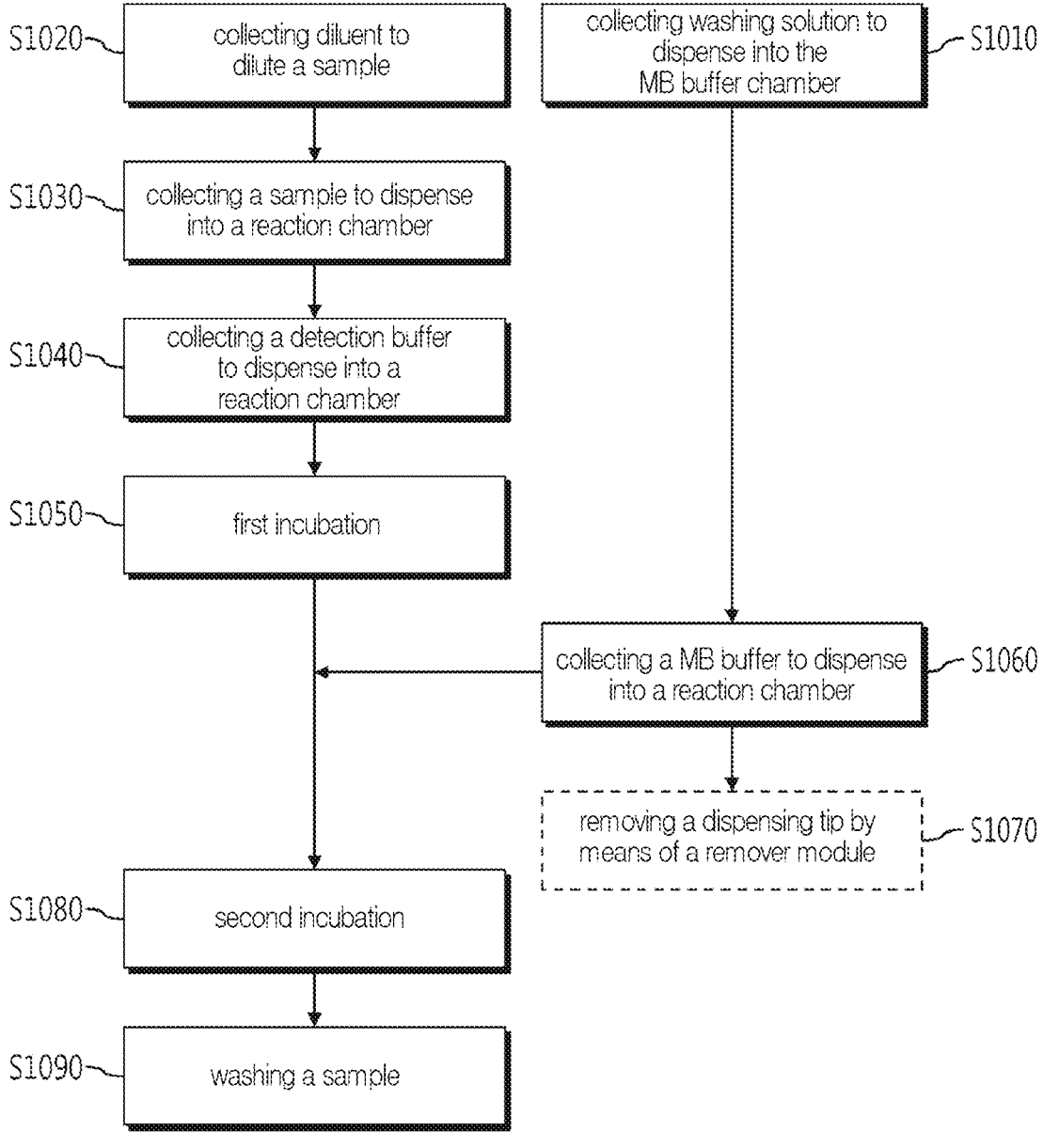
FIG. 20 is a flowchart showing in detail the sample dispensing process in the automated liquid immunoassay method according to an embodiment of the present invention.

FIG. 20 is a flowchart showing in detail the sample dispensing process in the automated liquid immunoassay method according to an embodiment of the present invention.

First, after the barcode is recognized, each of the seals of the cuvette 10 is punched by a punch arm 552 so as to be open. Subsequently, a dispensing tip 20 is fitted and fixed to the collection arm 556. And then, a predetermined volume of washing solution is collected from the first washing chamber 15a and dispensed into the MB buffer chamber 13a (S1010).

Subsequently, a predetermined diluent is collected from the dilution buffer chamber 13c, and dispensed into the sample chamber 12 (S1020). And then, a mixing process (3 times) is performed. Subsequently, a predetermined volume of the diluted sample is collected and dispensed into the reaction chamber 14 (S1030). And then, after the materials are mixed in the chamber 13b filled with the detection buffer, a predetermined volume of the solution is collected and dispensed into the reaction chamber 14 (S1040). And then, the solution is mixed (three times). Subsequently, the first incubation process is performed for a predetermined period of time at a specific temperature (S1050). Subsequently, after the materials are mixed in the MB buffer chamber 13a, a predetermined volume of the solution is collected in the MB buffer chamber 13a, dispensed into the reaction chamber 14 (S1060). And then the solution is mixed. Subsequently, the dispensing tip 20 is removed by means of the remover module 340 (S1070). And then, the dispensing tip 20 is placed in the dispensing tip fitting hole 21 of the cuvette where the reaction is performed. In addition, a second incubation process is performed for a predetermined period of time at a specific temperature (S1080).

Subsequently, a washing process is performed after the second incubation time (S1090). The washing process is performed as follows. The washing tip 30 is first fitted to the straw arm 554. And then, the magnetic beam 564 is introduced into the straw arm 554 so as to be introduced into the reaction chamber 14 for a predetermined period of time. And, after the magnetic beam 564 is introduced into the first washing chamber 15a, the magnetic beam 564 is moved vertically upward and downward several times so as to perform washing. Subsequently, the magnetic beam 564 is introduced into the straw arm 554 again. And then, the magnetic beam 564 is introduced into the second washing chamber 15b. And then, the magnetic beam 564 is moved vertically upward and downward several times to perform washing. Subsequently, the magnetic beam 564 is introduced into the straw arm 554 again and then introduced into the detection chamber 16 so as to remove the washing tip 30.

Subsequently, after a third incubation process performed for a predetermined period of time, an optical measurement process is performed. The result (concentration, etc.) obtained in the optical measurement may be output to a display and a printer.

Figure 21:
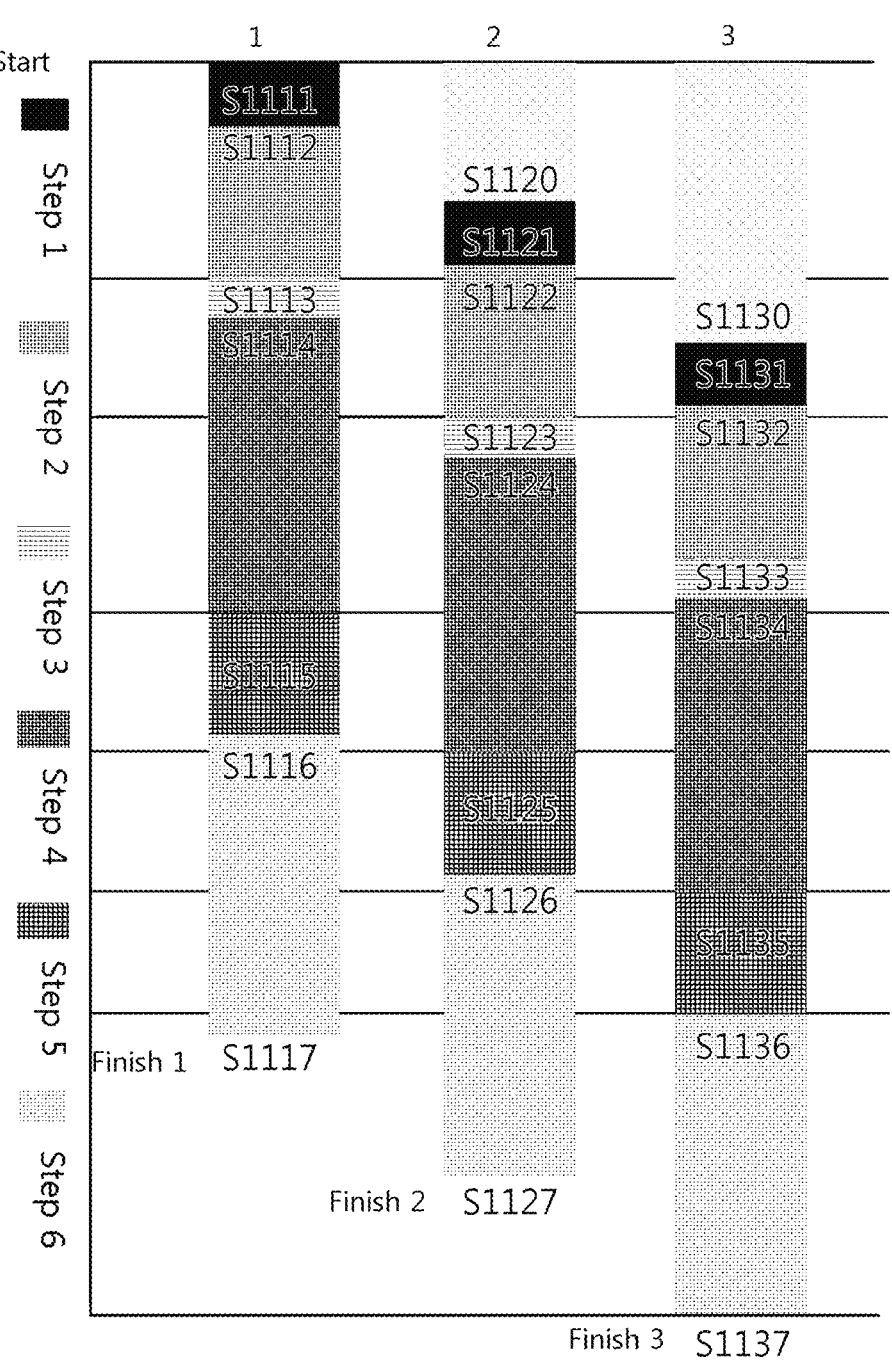
FIG. 21 is a timing diagram showing the operations of all cuvettes in case that three cuvettes are used in the automated liquid immunoassay method to according an embodiment of the present invention.

In addition, it is possible to perform a reaction in another cuvette during the incubation process. FIG. 21 is a timing diagram showing the operations of all cuvettes in case that three cuvettes are used in the automated liquid immunoassay method according to an embodiment of the present invention. FIG. 21 shows the order in which each step such as dispensing, washing, incubation, etc. is performed for three cuvettes.

Each step can be divided into Step 1, Step 2, Step 3, Step 4, Step 5, and Step 6. The Steps can be performed by dilution, collection, dispensing, mixing, washing, incubation, and measurement. Those Steps may be added or omitted depending on the purpose.

In order to drive and measure three types of cuvettes at the same time, all the steps should be separated from one another. FIG. 21 shows an example of a protocol for inspecting three types of cuvettes. The start point and the end points of each step are clearly separated from each other. Eventually, the time required to measure and inspect all three cuvettes can be significantly reduced. Especially, when preparation, dispensing or washing operation is performed in one cuvette during the incubation time of another cuvette, measurement time can be reduced.

For example, if it takes 20 minutes to inspect one cuvette, it usually takes more than 60 minutes to inspect three cuvettes. However, when using the above-mentioned method, it can take about 23 minutes or less to inspect three types of cuvettes with only one pump module, so that the time required for measurement and analysis can be reduced.

In order to perform the measurement process using a plurality of cuvettes without contamination between the cuvettes, a plurality of dispensing tips and washing tips are required to collect, dispense, and dilute reagents of each cuvette. The present invention includes a remover plate formed with depression and is designed to place a dispensing tip and a washing tip in the depression of each cuvette. After the tips used in collection, dispensing, and washing of the reagent in each cuvette are placed back to the depression of the corresponding cuvette, the dispensing tip and the washing tip of another cuvette are mounted to each holder so as to inspect multiple cuvettes simultaneously without contamination between cuvettes in a short time.

In the following embodiment, only a few examples are described for the replacement of the dispensing tip or the washing tip. However, it is desirable to remove the dispensing tip or the washing tip used in each cuvette before the operation of another cuvette, and mount the dispensing tip or the washing tip of the cuvette to be worked.

First, a sample is diluted and a reactant is added in the first cuvette for preparation (S1111). And then, the first incubation is started (S1112). The second cuvette which has been waiting (S1120) prepares in the same manner (S1121). The first incubation is started (S1122). Subsequently, when the first incubation of the first cuvette is finished, the dispensing operations such as adding magnetic beads (S1113). And then, a second incubation is started (S1114). Thereafter, the dispensing tip 20 used for dispensing the sample in the first cuvette is removed from the collection arm 556 and mounted on the first cuvette.

Then, the third cuvette waits. And then, the third cuvette which has been waiting (S1130) prepares (S1131). And then, the first incubation is started (S1132).

While the second incubation is performed in the first cuvette, the dispensing tip to be used for dispensing the sample in the second cuvette is mounted on the collection arm 556. And then, the dispensing operation such as addition of magnetic beads are performed in the second cuvette too (S1123). After that, the second incubation is started (S1124).

When the second incubation begins, the dispensing tip used for dispensing the sample in the second cuvette is removed from the collection arm 556.

Similarly, the dispensing operation is performed in the third cuvette (S1133). And then, the second incubation can be started (S1134).

Subsequently, during the incubations of the second cuvette and the third cuvette, the washing tip 30 to be used for washing the sample in the first cuvette is mounted on the straw arm 554. And then, when the second incubation of the first cuvette is finished, the washing operation is performed (S1115). And then, the third incubation is started (S1116). During the third incubation of the first cuvette, the washing operation is performed in the second cuvette too (S1125). And then, the third incubation is started (S1126). In the same way, the washing operation is performed in the third cuvette too (S1135). And then, the third incubation is started (S1136).

When the third incubation is finished in the first cuvette, the measurement is performed (S1117). When the third incubation is also finished in the second cuvette, the measurement is performed (S1127). Similarly, when the third incubation is also finished in the third cuvette, the measurement can be performed (S1137).

According to the automated liquid immunofluorescence assay device 1 according to an embodiment of the present invention, it is possible to detect/read the reaction product by use of dispensing and reaction of the sample, purification of the reaction product through a washing module using magnetic beads, and a liquid sample optical system with high sensitivity and high specificity, compared to the existing methods. Particularly, according to the present invention, the inspection for detection, reading and analysis of the reaction product can be performed accurately and quickly under one integrated system after the sample is distributed and the reagent is reacted with the sample. So, it reduces inspection time and improves the accuracy and reproducibility of the inspection. And, it reduces the number of steps involved in the overall inspection and the cost for inspection.

In addition, the arm unit 550 provided in the automated liquid immunofluorescence assay device 1 according to an embodiment of the present invention is provided with a punch arm 552, a collection arm 556 and a straw arm 554, and they are integrated into an all-in-one module. Therefore, when dispensing a pump, driving a puncher, washing, and separating a dispensing tip 20 from a washing tip 30, it is possible to control the positions of them vertically upward and downward with one driving motor. Therefore, unlike when each module is configured to be controlled by each driving motor separately, it is possible to reduce the size and the production cost. In addition, the arm unit 550 is configured into an all-in-one module. Each arm is connected to one vertical drive unit 544 and works but is designed to have no interference between drives. In this way, the arm unit 550 configured into an all-in-one module is used, so that it is possible to reduce the overall size and the manufacturing cost of the equipment.

In addition, the pump unit 506 included in the device according to an embodiment of the present invention adopts a motor capable of controlling a rotary micro-step so as to precisely adjust the amount when the samples, the reagents, or the reaction products are inhaled or discharged for separation and dispensing through a dispensing tip.

In addition, the device according to an embodiment of the present invention is provided with a remover module 340, so that the dispensing tip 20 and the washing tip 30 which have been used can be easily separated from the dispenser module

500. In addition, as the separation is made by the remover module 340, the dispensing tip 20 and the washing tip 30 can be reused after separation.

In addition, the device according to an embodiment of the present invention includes a standard block 360, so that inspection may be made using a standard fluorescence ratio to a standard fluorescence.

In summary, the device according to an embodiment of the present invention is an automated immunoassay device with convenience in which reagents are integrally prepared and reagents are not required to prepare. Multiple such as three different inspections can be performed at the same time. In the conventional case, only the same inspections can be performed at the same time. In addition, the device of the present invention adopts an integrated module that can perform all of punching, reagent distribution, dispensing and washing, and a system that can minimize the variation in optical systems and devices by use of the standard fluorescence. In addition, the reaction temperature of the reagent can be kept constant. And, the dispensing tip and the washing tip which are consumable can be remounted on the cuvette. So, there is no need for a separate space to discard the tip. In case that a device uses a dispensing tip and a washing tip which are consumable, it is configured to discard the dispensing tip after use. Because of contamination, it cannot be used for inspection on other reagents. In addition, the device according to an embodiment of the present invention needs to replace the dispensing tip to prepare for the reaction of another reagent during the reaction of a reagent in a first cuvette. Here, the used tip is seated on the first cuvette, and the preparation process is performed using the dispensing tips of second and third cuvettes. Thereafter, the dispensing tip of the first cuvette is remounted to prepare for a second incubation process. If discarded is the dispensing tip that has been used in the first incubation, a new tip should be adopted to prepare for the second incubation. The device is seated on the cartridge. And then, dispensing and mixing are performed in other cartridges. And then the tip of the original cartridge can be used again to perform the next process, so that demanded are only one dispensing tip and one washing tip which are consumable. In addition, there is no need to prepare the dispensing tip inside the device, so that it has spatial advantage and a more compact device can be designed.

The preferred embodiments of the present invention are described above in detail. However, the scope of the present invention is not limited thereto. Various modifications and improvements made by those skilled in the art using the basic concepts of the present invention defined in the following claims also belong to the rights range of the present invention.

The invention claimed is:

1. An automated liquid immunoassay device comprising a straw arm capable of fixing a washing tip to a lower part and having a hollow penetrating vertically upward and downward inside;

a magnetic beam positioned in the hollow of the straw arm and capable of moving vertically upward and downward relative to the straw arm;

a movable body to which the straw arm is fixed;

a movable body drive unit for moving the movable body;

a driving motor for moving the magnetic beam, the driving motor fixed to the moveable body such that movement of the moveable body moves the driving motor, the straw arm, and the magnetic beam together as an integrated unit;

a control unit for controlling the movable body drive unit;

a punch arm having a punch tip at a lower part thereof and fixed to the movable body, wherein a length between the movable body and the lower part of the punch arm is longer than a length between the movable body and the lower part of the straw arm, and wherein movement of the moveable body moves the driving motor, the straw arm, the magnetic beam, and the punch arm;

a collection arm capable of fixing a dispensing tip to a lower part thereof, having a hollow penetrating vertically upward and downward inside, and fixed to the movable body; and a remover plate comprising a remover hole in which a depression is formed, wherein the remover hole is configured to remove the dispensing tip from the collection arm, and the depression is recessed to a side of the remover hole to correspond to a position of the straw arm, and wherein, when the movable body is lowered toward the remover plate: (i) the washing tip fixed to the straw arm is seated in the depression such that the washing tip is not removed from the straw arm, and (ii) the dispensing tip fixed to the collection arm is caught by the remover hole such that the dispensing tip is separated from the collection arm.

2. The device of claim 1, wherein the magnetic beam is provided with a permanent magnet at a lower part thereof.

3. The device of claim 1, further comprising:

a holder having a slot-type mount channel capable of mounting one or more cuvettes, and an inspection hole penetrating vertically upward and downward; and a holder drive unit capable of adjusting a position of the holder.

4. The device of claim 3, wherein the holder includes a heat plate for keeping a cuvette at a constant temperature at a lower part thereof.

5. The device of claim 3, further comprising:

an optical reader having a light source, a beam splitter, lenses and a detector; and a reader drive unit capable of moving the optical reader to match an inspection hole of the holder.

6. The device of claim 3, wherein the holder includes a standard block having an optical hole penetrating in the vertical direction, and capable of mounting a fluorescence measurement standard material.

* * * * *